United States Patent
Frey et al.

(10) Patent No.: US 6,271,915 B1
(45) Date of Patent: Aug. 7, 2001

(54) OBJECTIVE MEASUREMENT AND CORRECTION OF OPTICAL SYSTEMS USING WAVEFRONT ANALYSIS

(75) Inventors: Rudolph W. Frey; James H. Burkhalter; Neil Zepkin; Edward Poppeliers; John A. Campin, all of Orlando, FL (US)

(73) Assignee: Autonomous Technologies Corporation, Orlando, FL (US)

( * ) Notice: Subject to any disclaimer, the term of this patent is extended or adjusted under 35 U.S.C. 154(b) by 0 days.

(21) Appl. No.: 09/664,128

(22) Filed: Sep. 18, 2000

Related U.S. Application Data

(63) Continuation of application No. 09/496,368, filed on Feb. 2, 2000, now abandoned, which is a continuation of application No. 08/756,272, filed on Nov. 25, 1996, now abandoned.

(51) Int. Cl.$^7$ .................................................. G01B 9/00
(52) U.S. Cl. ............................................................. 356/124
(58) Field of Search ................................. 356/124; 606/5

(56) References Cited

U.S. PATENT DOCUMENTS

| | | |
|---|---|---|
| 3,880,501 | 4/1975 | Munnerlyn . |
| 4,069,823 | 1/1978 | Isakov et al. . |

(List continued on next page.)

FOREIGN PATENT DOCUMENTS

| | | |
|---|---|---|
| 42 22 695 | 1/1994 | (DE) . |
| 0 697 611 A2 | 2/1996 | (EP) . |
| 0 697 611 A3 | 2/1996 | (EP) . |
| 5-146409 | 6/1993 | (JP) . |
| 6-327634 | 11/1994 | (JP) . |
| WO 87/05205 | 9/1987 | (WO) . |
| WO 87/06478 | 11/1987 | (WO) . |
| WO 92/01417 | 2/1992 | (WO) . |
| 95/28989 | 11/1995 | (WO) . |
| WO 98/27863 | 7/1998 | (WO) . |

OTHER PUBLICATIONS

Junzhong Liang, Bernhard Grimm, Stefan Goelz and Josef F. Bille, Objective measurement of wave aberrations of the human eye with the use of Hartmann–Shack wavefront sensor, J. Opt. Soc. Am. A. vol. 11, No. 7, pp. 1949–1957, Jul. 1994.*

Pullianto, et al., "High–Speed Photography of Excimer Laser Ablation of the Cornea,"*Arch Ophithalmol*, vol. 105, Sep. 1987, pp. 1255–1259.

Liang, et al., "Objective Measurement of Wave Aberrations of the Human Eye with the Use of a Hartmann–Shack Wave–front Sensor," *J. Opt. Soc. Am. A*, vol. 11, No. 7, Jul. 1994, pp. 1949–1957.

(List continued on next page.)

Primary Examiner—Frank G. Font
Assistant Examiner—Amanda Merlino
(74) Attorney, Agent, or Firm—Allen, Dyer, Doppelt, Milbrath & Gilchrist, P.A.

(57) ABSTRACT

Vision in an eye is corrected using an energy source for generating a beam of optical radiation and focusing optics disposed in the path of the beam for directing the beam through the eye, where the beam is reflected back from the retina of the eye as a wavefront of radiation to be measured. An optical correction based on an optical path difference between the measured wavefront and a desired plane wave, and refractive indices of the media through which the wavefront passes is provided to a laser delivery system with a laser beam sufficient for ablating corneal material from the cornea of the eye. The laser beam is directed at selected locations on the cornea for ablating the corneal material in response to the optical correction to cause the measured wavefront to approximate the desired plane wave, and thus provide an optical correction.

43 Claims, 9 Drawing Sheets

U.S. PATENT DOCUMENTS

| | | |
|---|---|---|
| 4,523,821 | 6/1985 | Lang et al. . |
| 4,579,430 | 4/1986 | Bille . |
| 4,632,528 | 12/1986 | Yoshino et al. . |
| 4,669,466 | 6/1987 | L'Esperance . |
| 4,688,941 | 8/1987 | Philbert . |
| 4,702,245 | 10/1987 | Schröder et al. . |
| 4,718,418 | 1/1988 | L'Esperance, Jr. . |
| 4,721,379 | 1/1988 | L'Esperance . |
| 4,729,372 | 3/1988 | L'Esperance, Jr. . |
| 4,750,818 | 6/1988 | Cochran . |
| 4,764,930 | 8/1988 | Bille et al. . |
| 4,838,679 | 6/1989 | Bille . |
| 4,848,340 | 7/1989 | Bille et al. . |
| 4,881,808 | 11/1989 | Bille et al. . |
| 4,901,718 | 2/1990 | Bille et al. . |
| 4,907,586 | 3/1990 | Bille et al. . |
| 4,941,093 | 7/1990 | Marshall et al. . |
| 4,972,836 | 11/1990 | Schenck et al. . |
| 4,988,348 | 1/1991 | Bille . |
| 4,991,953 | 2/1991 | Pfibsen et al. . |
| 5,026,977 | 6/1991 | Hubbard, Jr. . |
| 5,062,702 | 11/1991 | Bille . |
| 5,106,183 | 4/1992 | Yoder, Jr. . |
| 5,114,628 | 5/1992 | Höfer et al . . |
| 5,139,022 | 8/1992 | Lempert . |
| 5,147,352 | 9/1992 | Azema et al. . |
| 5,159,361 | 10/1992 | Cambier et al. . |
| 5,177,511 | 1/1993 | Feuerstein et al. . |
| 5,184,157 | 2/1993 | Ichihashi et al. . |
| 5,196,006 | 3/1993 | Klopotek et al. . |
| 5,198,845 | 3/1993 | Triller . |
| 5,202,709 | 4/1993 | Ischihashi et al. . |
| 5,214,456 | 5/1993 | Gersten . |
| 5,221,834 | 6/1993 | Lisson et al. . |
| 5,229,889 | 7/1993 | Kittell . |
| 5,233,174 | 8/1993 | Zmek . |
| 5,243,367 | 9/1993 | Spellitz . |
| 5,246,435 | 9/1993 | Bille et al. . |
| 5,258,791 | 11/1993 | Penney et al. . |
| 5,263,950 | 11/1993 | L'Esperance, Jr. . |
| 5,279,611 | 1/1994 | McDonnell et al. . |
| 5,293,871 | 3/1994 | Reinstein et al. . |
| 5,298,971 | 3/1994 | Huang et al. . |
| 5,307,097 | 4/1994 | Baker . |
| 5,324,281 | 6/1994 | Muller . |
| 5,334,190 | 8/1994 | Seiler . |
| 5,339,121 | 8/1994 | Shimmick et al. . |
| 5,360,424 | 11/1994 | Klopotek . |
| 5,395,356 | 3/1995 | King et al. . |
| 5,404,884 | 4/1995 | Lempert . |
| 5,410,376 | 4/1995 | Cornsweet et al. . |
| 5,411,501 | 5/1995 | Klopotek . |
| 5,423,801 | 6/1995 | Marshall et al. . |
| 5,437,658 | 8/1995 | Muller et al. . |
| 5,439,462 | 8/1995 | Bille et al. . |
| 5,442,412 | 8/1995 | Frey et al. . |
| 5,452,031 | 9/1995 | Ducharme . |
| 5,461,212 | 10/1995 | Seiler et al. . |
| 5,473,392 | 12/1995 | Klopotek . |
| 5,474,548 | 12/1995 | Knopp et al. . |
| 5,475,452 | 12/1995 | Kuhn et al. . |
| 5,491,524 | 2/1996 | Hellmuth et al. . |
| 5,493,391 | 2/1996 | Neal et al. . |
| 5,502,518 | 3/1996 | Lieberman . |
| 5,505,723 | 4/1996 | Muller . |
| 5,507,741 | 4/1996 | L'Esperance, Jr. . |
| 5,512,965 | 4/1996 | Snook . |
| 5,512,966 | 4/1996 | Snook . |
| 5,521,657 | 5/1996 | Klopotek . |
| 5,548,354 | 8/1996 | Kasahara et al. . |
| 5,556,395 | 9/1996 | Shimmick et al. . |
| 5,563,709 | 10/1996 | Poultney . |
| 5,570,142 | 10/1996 | Lieberman . |
| 5,581,347 | 12/1996 | Le Saux et al. . |
| 5,592,246 | 1/1997 | Kuhn et al. . |
| 5,629,765 | 5/1997 | Schmutz . |
| 5,632,282 | 5/1997 | Hay et al. . |
| 5,632,742 | 5/1997 | Frey et al. . |
| 5,673,096 | 9/1997 | Dorsel et al. . |
| 5,684,545 | 11/1997 | Dou et al. . |
| 5,711,762 | 1/1998 | Trokel . |
| 5,722,427 | 3/1998 | Wakil et al. . |
| 5,735,283 | 4/1998 | Snook . |
| 5,735,843 | 4/1998 | Trokel . |
| 5,740,803 | 4/1998 | Gray et al. . |
| 5,757,463 | 5/1998 | Kohayakawa . |
| 5,777,719 | 7/1998 | Williams et al. . |
| 5,784,146 | 7/1998 | Nanjo et al. . |
| 5,785,704 | 7/1998 | Bille et al. . |
| 5,822,035 | 10/1998 | Bille . |
| 5,825,476 | 10/1998 | Abitol et al. . |
| 5,825,746 | 10/1998 | Lee . |
| 5,841,511 | 11/1998 | D'Souza et al. . |
| 5,847,804 | 12/1998 | Sarver et al. . |
| 5,861,955 | 1/1999 | Gordon . |
| 5,864,381 | 1/1999 | Neal et al. . |
| 5,920,373 | 7/1999 | Bille . |
| 5,936,720 | 8/1999 | Neal et al. . |
| 5,943,117 | 12/1999 | Van De Velde . |
| 5,949,521 | 9/1999 | Williams et al . . |
| 5,963,300 | 10/1999 | Horwitz . |
| 5,966,197 | 10/1999 | Yee . |
| 6,007,204 | 12/1999 | Fahrenkrug et al. . |
| 6,095,651 | 8/2000 | Williams et al. . |

OTHER PUBLICATIONS

Wu, "Supernormal Vision, a Focus on Adaptive Optics Improves Image of the Eye and Boosts Vision," *Science News*, vol. 152, Nov. 15, 1997, pp. 312–313.

Dreher, et al., "Active Optical Depth Resolution Improvement of the Laser Tomographic Scanner", *Applied Optics*, vol. 28, No. 4, Feb. 1989, pp. 804–808.

Geary, "Appendix 1.1—Basic Geometrical Optics, Chapter 6—Indirect Wavefront Measurement, Part II,"and "Chapter 7—Wavefront Sensor Characterization & Calibration," *Introduction to Wavefront Sensors*, May 1995, pp. 10–11, 89–103, and 105–109.

"Scientists Snap Sharpest Pictures of Living Human Retina," http://www.rochester.edu/pr/releases/opt/will.htm, Oct. 3, 1994.

The Applied Optics Group, "Shack Hartmann Sensors." http://op.ph.ic.ac.uk/ao/sh sense.html, Jun. 4, 1996, pp. 1–3.

The Applied Optics Group, "Results from UKIRT", http://op.ph.ic.ac.uk/ao/ukirt res.html, Feb. 22, 1995, pp. 1–2.

The Applied Optics Group, "Astronomical Imaging Through Turbulence: An Overview," http://op.ph.ic.ac.uk/ao/overview.html Jun. 4, 1996, pp. 1–4.

.eESA, WFS, "Wave Front Sensor," http://esapub.esrin.esa.it/pointtotest/test251.html, May 23, 1997, pp. 1–2.

Williams, "Limits of Human Vision," http://www.cvs.rochester.edu/people/d williams/d williams.html, Dec. 30, 1998, pp. 1–4.

"Extensions of Low–Cost Adaptive Optics: Imaging of Space–Objects, the Retina, and Power Projection," Industrial Sensors and Actuators, dated Dec. 1993 (actual publication date, if any, unknown), pp. 1, 10, and 15.

Labjuhn, et al., Astigmatismuskorrektur durch Laserthermokeratoplastik (LTK)—Ein Ansatz für die Korrektur des hohen Astigmatismus nach Perforierender Keratoplastik, *Contactologia 18D* (1996), pp. 175–183.

Cohen, et al., "Assessment of the Power and Height of Radial Aspheres Reported by a Computer–assisted Keratoscope," *American Journal of Ophthalmology*, vol. 119, vol. No. 6, Nov. 30, 1994, pp. 723–732.

Corbett, et al., "The Topography of the Normal Cornea," *Eur J Implant Ref Surg.*, vol. 6, Oct., 1994, pp. 286–297.

Maeder, et al., "Accurate 3D Corneal Surface Measurement Using an Automated Mapping Approach," SPIE, vol. 2434, 1995, pp. 328–334.

Salmon, et al., "Comparison of Elevation, Curvature, and Power Descriptors for Corneal Topographic Mapping," *Optometry & Vision Science*, vol. 72, No. 11, 1195, pp. 800–808.

Pavlopoulos, et al., "The Effect of Artificial Tears on Computer–assisted Corneal Topography in Normal Eyes and After Penetrating Keratoplasty," *American Journal of Ophthalmology*, vol. 119, Jun. 1995, pp. 712–722.

Roberts, "Characterization of the Inherent Error in a Spherically–Biased Corneal Topography System in Mapping a Radially Aspheric Surface," *Journal of Refractive & Corneal Surgery*, vol. 10, Mar./Apr. 1994, pp. 103–111.

Thornton, "Clinical Evaluation of Corneal Topography," *J. Cataract Refract. Surg.*, vol. 19, Supplement 1993, pp. 198–202.

Rabinowitz, et al., "Computer–assisted Corneal Topography in Keratoconus," *Refractive & Corneal Surgery*, vol. 5, Nov./Dec. 1989, pp. 400–408.

Wilson, et al., "Accuracy and Precision of the Corneal Analysis System and the Topographic Modeling System," *Cornea*, vol. 11, No. 1, 1992, pp. 28–35.

Bogan, et al., Computer–assisted Videokeratography of Corneal Topography After Radial Keratotomy, *Arch. Ophthalmol.*, vol. 109, Jun. 1991, pp. 834–841.

Bogan, et al., "Classification of Normal Corneal Topography Based on Computer–assisted Videokeratography." *Arch. Ophtalmol.*, vol. 108, Jul. 1990, pp. 945–949.

Reidy, et al., "The Corneal Topography of Epikeratophakia," *Refractive & Corneal Surgery*, vol. 6, Jan./Feb. 1990, pp. 26–31.

Dingeldein, et al., "The Topography of Normal Corneas," *Arch. Ophthalmol*, vol. 107, Apr. 1989, pp. 512–518.

McDonnell, et al., "Topographic Analysis and Visual Acuity After Radial Keratotomy," *American Journal of Ophthalmology*, vol. 106, No. 6, Dec. 1988, pp. 692–695.

McDonnell, et al., "Corneal Topographic Changes After Radial Keratotomy," *Ophthalmology*, vol. 96, No. 1, Jan. 1989, pp. 45–49.

Kiely, et al., "The Mean Shape of the Human Cornea," *Optica Acta*, vol. 29, No. 8, 1982, pp. 1027–1040.

Bafna, et al., "Corneal Power Calculated by the Paraxial Formula and Snell's Law in Normal Corneas," *Investigative Ophthalmology & Visual Science*, vol. 37, No. 3, Feb. 1996, Poster No. 2589.

Matallana, et al., "3–D Video Corneal Topography True Elevation Mapping," *Investigative Ophthalmology & Visual Science*, vol. 37, No. 3, Feb. 1996, Poster No. 2590.

Aoyama, et al, "Quantitative Evaluation of Corneal Astigmatism Using Computer Corneal Topography and Newly Developed Software," *Investigative Ophthalmology & Visual Science*, vol. 37, No. 3, Feb. 1996, Poster No. 2591.

Celikkol, et al, "Neural Network Analysis of Videokeratography Following Excimer Laser Photorefractive Keratectomy," *Investigative Ophthalmology & Visual Science*, vol. 37, No. 3, Feb. 1996, Poster No. 2592.

Walsh, et al., "Objective Technique for the Determination of Monochromatic Aberrations of the Human Eye," *J. Opt. Soc. Am. A*, vol. 1, No. 9, Sep. 1984, pp. 987–992.

Williams, et al., "Adaptive Optics for High Resolution Retinal," *Investigative Ophthalmology & Visual Science*, vol. 37, No. 3, Feb. 1996, p. 1055.

Charman, "Wavefront Aberration of the Eye: A Review," *Optometry and Vision Science*, vol. 68, No. 8, pp. 574–583.

Bartsch, et al., "Resolution Improvement in Confocal Scanning Laser Tomography of the Human Fundus," *1994 Technical Digest Series*, vol. 2 (Optical Society in America, Washington D. C.), 1994, pp. 134–137.

Dreher, et al., "Active Optical Depth Resolution Improvement of the Laser Tomographic Scanner," *Applied Optics*, vol. 28, No. 4, Feb. 1989, pp. 804–808.

Bille, et al., "Scanning Laser Tomography of the Living Human Eye," *Noninvasive Diagnostic Techniques in Ophthalmology*, Chapter 28, edited by Masters, B.R., Springer–Verlag, 1990, pp. 528–547.

* cited by examiner

OBJECTIVE MEASUREMENT AND CORRECTION OF OPTICAL SYSTEMS USING WAVEFRONT ANALYSIS

CROSS-REFERENCE TO RELATED APPLICATIONS

This application is a continuation of and incorporates by reference application Ser. No. 09/496,368 now abandoned, filed Feb. 2, 2000, which itself is a continuation of abandoned application Ser. No. 08/756,272, filed Nov. 25,1996, all commonly owned with the present application.

FIELD OF THE INVENTION

The invention relates generally to optical aberration measurement and correction, and more particularly to the objective measurement and correction of optical systems having a real image focus such as human and animal eyes.

BACKGROUND OF THE INVENTION

Optical systems having a real image focus can receive collimated light and focus it at a point. Such optical systems can be found in nature, e.g., human and animal eyes, or can be man-made, e.g., laboratory systems, guidance systems, etc. In either case, aberrations in the optical system can affect the system's performance. By way of example, the human eye will be used to explain this problem.

Referring to FIG. 1A, a perfect or ideal eye 100 is shown diffusely reflecting an impinging light beam (not shown for sake of clarity) from the back of its retina 102 (i.e., the fovea centralis 103) through the eye's optics to include lens 104 and cornea 106. For such an ideal eye in a relaxed state, i.e., not accommodating to provide near-field focus, the reflected light (represented by arrows 108) exits eye 100 as a sequence as of plane waves, one of which is represented by straight line 110. However, an eye normally has aberrations that cause deformation or distortion of the wave exiting the eye. This is shown by way of example in FIG. 1B where aberrated eye 120 diffusely reflects an impinging light beam (again not shown for sake of clarity) from the back of its retina 122 of the fovea centralis 123 through lens 124 and cornea 126. For aberrated eye 120, reflected light 128 exits eye 120 as a sequence of distorted wavefronts, one of which is represented by wavy line 130.

Currently, there are a number of technologies that attempt to provide the patient with improved visual acuity. Examples of such technologies include remodeling of cornea 126 using refractive laser surgery or intra-corneal implants, and adding synthetic lenses to the optical system using intraocular lens implants or precision-ground spectacles. In each case, the amount of corrective treatment is typically determined by placing spherical and/or cylindrical lenses of known refractive power at the spectacle plane (approximately 1.0–1.5 centimeters anterior to cornea 126) and asking the patient which lens or lens combination provides the clearest vision. This is obviously a very imprecise measurement of the true distortions in wavefront 130 because 1) a single spherocylindrical compensation is applied across the entire wavefront, 2) vision is tested at discrete intervals (i.e., diopter units) of refractive correction, and 3) subjective determination by the patient is required in order to determine the optical correction. Thus, the conventional methodology for determining refractive errors in the eye is substantially less accurate than the techniques now available for correcting the ocular aberrations.

One method of measuring ocular refractive errors is disclosed by Penney et al. in "Spatially Resolved Objective Autorefractometer," U.S. Pat. No. 5,258,791, issued Nov. 2, 1993. Penney et al. teach the use of an autorefractometer to measure the refraction of the eye at numerous discrete locations across the corneal surface. The autorefractometer is designed to deliver a narrow beam of optical radiation to the surface of the eye, and to determine where that beam strikes the retina using a retinal imaging system. Both the angle of the beam's propagation direction with respect to the optical axis of the system and the approximate location at which the beam strikes the corneal surface of the eye are independently adjustable. A small uncertainty or error in the location of the beam's point of incidence on the cornea exists due to the curved corneal surface. For each point of incidence across the corneal surface, the refraction of the eye corresponding to that surface point can be determined by adjusting the angle at which the beam strikes the cornea until the beam refracted on to the iris strikes the fovea centralis. Adjustment of the beam angle of propagation can be accomplished either manually by the patient or automatically by the autorefractometer if a feedback loop involving a retinal imaging component is incorporated.

Penney et al. further teach the use of the autorefractometer measurements in determining the appropriate corneal surface reshaping to provide emmetropia. This is accomplished by first obtaining accurate measurement of corneal surface topography (using a separate commercially available device). A mathematical analysis is then performed using the initial corneal topography at each surface reference point, the measured refraction at each surface point, and Snell's law of refraction, to determine the required change in surface contour at each reference point. The contour changes at the various reference points are then combined to arrive at a single reshaping profile to be applied across the full corneal surface.

The major limitation to the approach described by Penney et al. is that a separate measurement of corneal topography is required to perform the Snell's Law analysis of needed refraction change. This requirement adds significantly to the time and cost of the complete diagnostic evaluation. Furthermore, the accuracy of the refraction change analysis will be dependent on the accuracy of the topographic measurement and the accuracy of the autorefractometer measurement. In addition, any error in the spatial orientation of the topography "map" with respect to the refraction map will degrade the accuracy of the needed correction profile.

A second limitation to the approach described by Penney et al. is that test points on the corneal surface are examined sequentially. Eye motion during the examination, either voluntary or involuntary, could introduce substantial errors in the refraction measurement. Penney et al. attempt to provide detection of such eye movement by deliberately including measurement points outside the pupil, i.e., in the corneal region overlying the iris, where the return from the retina will obviously be zero at specific intervals in the examination sequence. However, this approach may still allow substantial undetected eye movement error between such iris reference points.

At present, no corrective method is based on the concurrent examination of the complete distortions in wavefront 130. Measurement of wave aberrations of the human eye, i.e., ocular aberrations, has been studied for a number of years. One prior art method and system are disclosed by Liang et al. in "Objective Measurement of Wave Aberrations of the Human Eye With the Use of a Hartmann-Shack Wave-front Sensor," Journal of the Optical Society of America, Volume 11, No. 7, July 1994, p.p. 1949–1957. Liang et al. teach the use of a Hartmann-Shack wavefront sensor to measure ocular aberrations by measuring the wavefront emerging from the eye by the retinal reflection of a focused laser light spot on the retina's fovea. The actual wavefront is reconstructed using wavefront estimation with Zernike polynomials.

The Hartmann-Shack wavefront sensor disclosed by Liang et al. includes two identical layers of cylindrical lenses with the layers arranged so that the lenses in each layer are perpendicular to one another. In this way, the two layers act like a two-dimensional array of spherical lenslets that divide the incoming light wave into subapertures. The light through each subaperture is brought to focus in the focal plane of the lens array where a charge coupled device (CCD) image module resides.

The system of Liang et al. is calibrated by impinging an ideal plane wave of light on the lenslet array so that a reference or calibrating pattern of focus spots is imaged on the CCD. Since the ideal wavefront is planar, each spot related to the ideal wavefront is located on the optical axis of the corresponding lenslet. When a distorted wavefront passes through the lenslet array, the image spots on the CCD are shifted with respect to the reference pattern generated by the ideal wavefront. Each shift is proportional to the local slopes, i.e., partial derivatives, of the distorted wavefront which can be used to reconstruct the distorted wavefront, by means of modal wavefront estimation with Zernike polynomials.

However, the system disclosed by Liang et al. is effective only for eyes having fairly good vision. Eyes that exhibit considerable myopia (near-sightedness) would cause the focus spots to overlap on the CCD thereby making local slope determination impossible for eyes having this condition. Similarly, eyes that exhibit considerable hyperopia (farsightedness) deflect the focus spots such that they do not impinge on the CCD thereby again making local slope determination impossible for eyes having this condition.

Another limitation of the system of Liang et al. is the configuration of the Hartmann-Shack sensor in that the lenses must be uniform in order to define a uniform lenslet array so that the entire array shares a common focal plane and does not itself induce distortions in the wavefront. However, the manufacturing costs associated with such constraints are considerable.

Thus, owing to all of the above-noted limitations, Liang et al. can only achieve wavefront measurement for a relatively small class of patients. Such patients can have, at most, mildly distorted vision.

SUMMARY OF THE INVENTION

It is an object of the present invention to provide a method and system for objectively measuring aberrations of optical systems by wavefront analysis and for using such measurement to generate an optical correction.

Another object of the present invention is to provide for the objective measurement of ocular aberrations having a dynamic range that can cope with large amounts of such aberrations so as to be useful in practical applications.

Still another object of the present invention to provide a method and system for objectively measuring ocular aberrations using a wavefront analyzer of simple and inexpensive design.

It is further an object to correct vision by ablating corneal material using a laser beam directed to locations on the surface of the cornea of the eye in response to the objective measurements, thereby providing a measured wavefront that approximates a desired wavefront such as a plane wave.

Other objects and advantages of the present invention will become more obvious hereinafter in the specification and drawings.

To meet such objects, an optical correction system for correcting visual defects of an eye is provided which includes a wavefront analyzer disposed in the path of a wavefront emanating from the eye for determining an optical path difference between a plane wave and the wavefront, a converter for providing an optical correction based on the path difference and refractive indices of media through which the wavefront passes, and a laser beam having power sufficient for ablating corneal material of the cornea of the eye, wherein the optical correction is achieved by the removal of a selected amount of the corneal material.

A method aspect of the invention includes enhancing vision of an eye by optically correcting the eye based on an optical path difference between a plane wave and a wavefront emanating from the retina of the eye and refractive indices of media through which the wavefront passes, to thereby cause the wavefront to approximate the shape of the plane wave. Further, corneal surface altering is based on a Zernike reconstruction of the wavefront, and the optically correcting includes dividing the optical path difference by a difference between an index of refraction of corneal material and an index of refraction of air. The cornea is then ablated using a laser beam directed at selected locations on the surface of the cornea for altering the corneal surface of the eye without regard to a resulting topography of the surface of the cornea.

In accordance with the present invention, an energy source generates a beam of radiation. Optics, disposed in the path of the beam, direct the beam through a focusing optical system, e.g., an eye, that has a rear portion thereof functioning as a diffuse reflector. The beam is diffusely reflected back from the rear portion as a wavefront of radiation that passes through the focusing optical system to impinge on the optics. The optics project the wavefront to a wavefront analyzer in direct correspondence with the wavefront as it emerges from the focusing optical system. A wavefront analyzer is disposed in the path of the wavefront projected from the optics and calculates distortions of the wavefront as an estimate of ocular aberrations of the focusing optical system. The wavefront analyzer includes a wavefront sensor coupled to a processor that analyzes the sensor data to reconstruct the wavefront to include the distortions thereof.

In one embodiment, the radiation is optical radiation and the wavefront sensor is implemented using a plate and a planar array of light-sensitive cells. The plate is generally opaque but that has an array of light transmissive apertures that selectively let impinging light therethrough. The plate is disposed in the path of the wavefront so that portions of the wavefront pass through the light transmissive apertures. The planar array of cells is arranged parallel to and spaced apart from the plate by a selected distance. Each portion of the wavefront passing through one of the light transmissive apertures illuminates a geometric shape covering a unique plurality of cells. In another embodiment, the wavefront sensor comprises a two-dimensional array of spherical lenslets and a planar array of cells. The array of lenslets defines a focal plane that is a focal length away therefrom. The array of lenslets is disposed in the path of the wavefront where portions of the wavefront pass therethrough. The planar array of cells is arranged parallel to and spaced apart from the array of lenslets by a selected distance independent of the focal length. Similar to the first embodiment wavefront sensor, each portion of the wavefront illuminates a geometric shape covering a unique plurality of cells. Regardless of which wavefront sensor is used, the distance between the planar array of cells and the opaque plate, or the array of lenslets, can be varied to adjust the slope measurement gain of the wavefront sensor and thereby improve the dynamic range of the system.

Another measure of dynamic range enhancement is provided by the focusing optics. The focusing optics includes first and second lenses maintained in fixed positions in the path of the beam and wavefront. An arrangement of optical elements is disposed between the lenses in the path of the beam and the wavefront. The optical elements are adjustable to change the optical path length between the lenses.

If an optical correction is desired, the distortions are converted to an optical correction which, if placed in the path of the wavefront, causes the wavefront to appear approximately as a plane wave. The optical correction can be in the form of a lens or an amount of corneal material ablated from the eye.

DETAILED DESCRIPTION OF THE INVENTION

By way of illustrative example, the present invention will be described with respect to diagnosing and correcting a human eye. However, it is to be understood that the teachings of the present invention are applicable to any optical system having a real image focus that can (or can be adapted to) diffusely reflect a focused spot of radiation from a rear portion of the optical system back through the optical system as a wavefront of radiation. Thus, the present invention can be used with human or animal eyes of patients that may be alive or dead, or any man-made optical system satisfying the criteria regarding the real image focus.

Figure 1A:
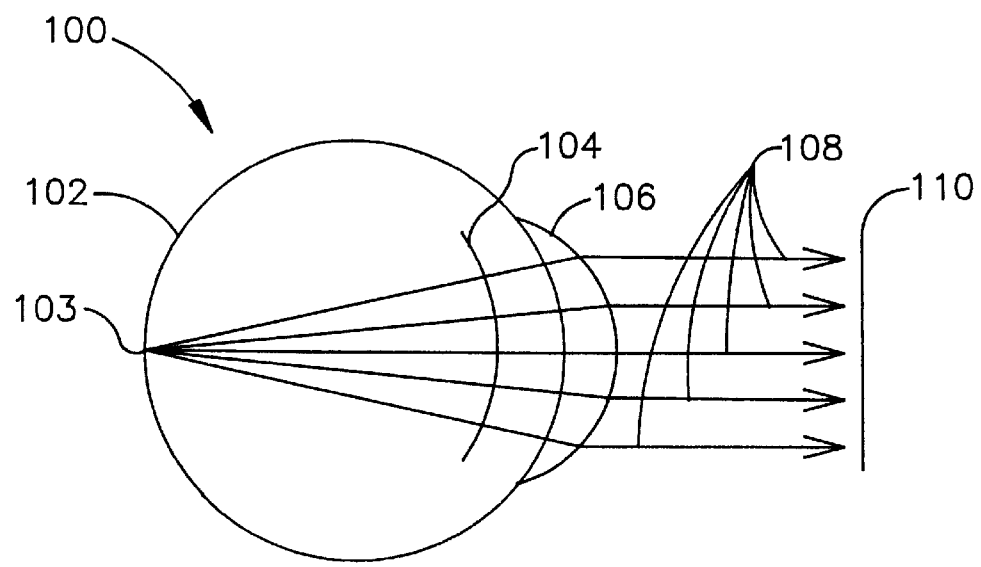
FIG. 1A is a schematic view of the ideal eye reflecting light from its retina as a planar wavefront.
Figure 1B:
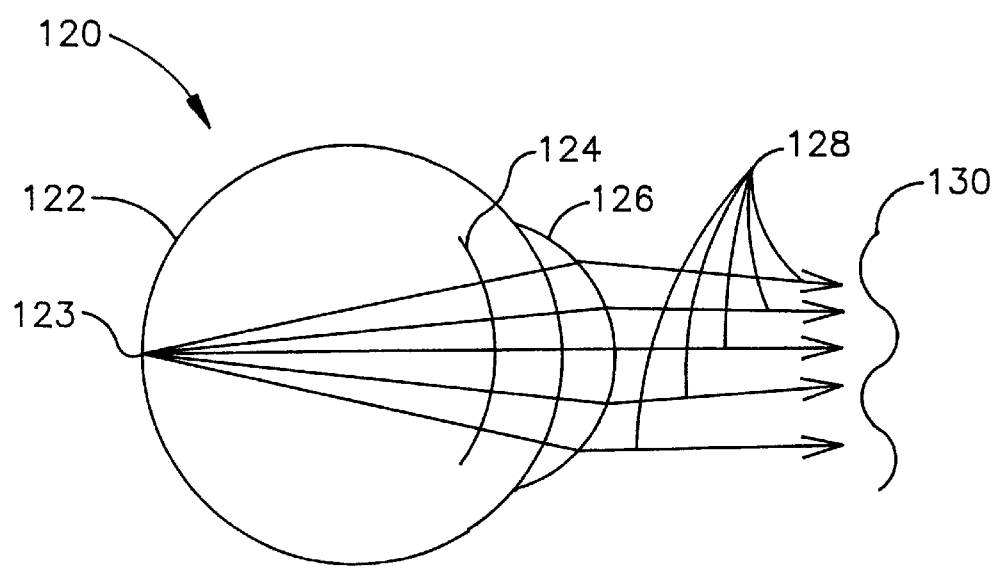
FIG. 1B is a schematic view of an aberrated eye reflecting light from its retina as a deformed wavefront.
Figure 1C:
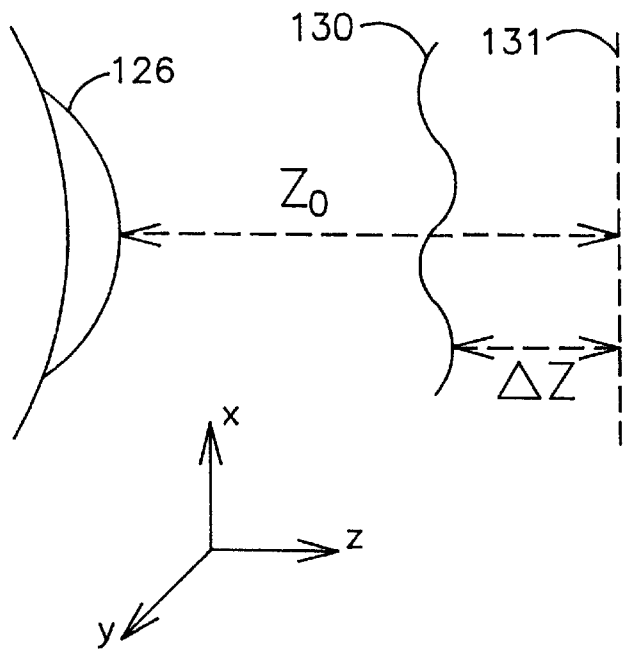
FIG. 1C is a schematic view of the distorted wavefront relative to a reference plane to show the wavefront error or optical path difference as a function of transverse distance in the propagation direction.

The method of using wavefront analysis to determine an appropriate optical correction will be introduced with reference to the eye example and the aid of the schematic shown in FIG. 1C. For convenience, a coordinate system is defined where positive x is upward in the plane of the figure, positive y is outward from the plane of the figure, and positive z is to the right along the propagation direction. Distorted wavefront 130 can be described mathematically as $W(x,y)$.

One method of measuring the distortions in wavefront 130 is to determine the spatial separation $\Delta z$ between a reference plane 131 (analogous to ideal wavefront 110) at a known distance $z_O$ from the eye at each $(x,y)$ point of distorted wavefront 130 as the leading edge of wavefront 130 traverses distance $z_O$. This is illustrated in FIG. 1C and is described mathematically as $$\Delta z(x,y) = z_0 - W(x,y) \qquad (1)$$

These $\Delta z$ measurements define the inappropriate optical path differences due to the aberrations in the test eye. The appropriate correction consists of removing these optical path differences. Ideally, such correction is performed at reference plane 131.

Depending on the corrective therapy (i.e., corneal tissue ablation, synthetic lens addition, etc.), the amount of material removed or added at each $(x,y)$ coordinate can be calculated directly if the refractive index of the material in question is known. For many procedures, such as intra-ocular lens implantation or radial keratotomy, such wavefront analysis can be performed repetitively during the procedure to provide feedback information as to the appropriate endpoint of the procedure.

Figure 1D:
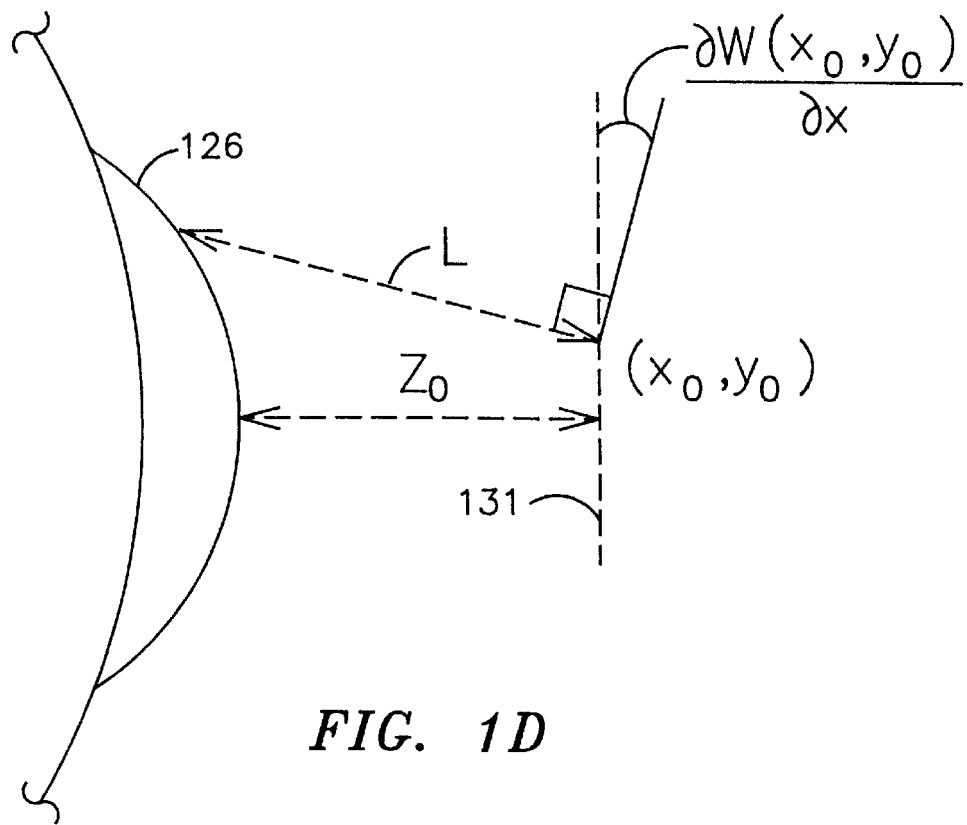
FIG. 1D is a schematic view of the distorted wavefront relative to a reference plane that is tangent to the surface of the cornea.

In terms of the illustrative example, the differences $\Delta z(x,y)$ between the distorted and ideal wavefronts are the consequence of the aberrations in the eye. Ideal correction of those aberrations consists of introducing an optical path difference at reference plane 131 of negative $\Delta z(x,y)$. If the treatment approach consists of removing tissue from the surface of the cornea by laser ablation, then a logical choice for the location of reference plane 131 is tangential to the surface of cornea 126 (i.e., $z_O=0$). This is shown schematically in FIG. 1D where the curvature of cornea 126 is greatly exaggerated for clarity of illustration. Ablation could then be carried out discretely at each $(x,y)$ coordinate along the cornea by a laser beam delivery and eye tracking system such as disclosed in U.S. patent application Ser. No. 08/232, 615, filed Apr. 25, 1994, owned by the same assignee as the present invention, and which is incorporated herein by reference.

The appropriate corneal ablation depth at any $(x,y)$ transverse coordinate is, to within a small error, given by $$\Delta z(x,y)/(n_c-1) \qquad (2)$$

where $n_c$ is the refractive index of corneal tissue or 1.3775. The method described in detail below calculates $\Delta z(x,y)$ by first measuring the local slopes in wavefront 130, i.e., $\delta W(x,y)/\delta x$ and $\delta W(x,y)/\delta y$, at a number of points in the transverse x and y directions in reference plane 131 and then generating a mathematical description of $W(x,y)$ having slopes in best possible agreement with the experimentally determined values. One such slope $\delta W(x_O,y_O)/\delta x$ is referenced in FIG. 1D. In doing this, a small error is introduced due to the fact that distorted wavefront 130 is measured at reference plane 131 while wavefront 130 emerged from a curved (corneal) surface just posterior to reference plane 131. This error is similar to that encountered with the prior art method of Penney et al. discussed above. The error $E_x(x,y)$ is the lateral displacement in the x-direction at each (x,y) location at the measurement plane (i.e., reference plane 131) to the curved corneal surface. A similar error will be manifest for any corrections involving curved optical surfaces. The error will generally increase with both (x,y) displacement from the point of tangency and local wavefront error.

The magnitude of error $E_x(x,y)$ can be found for each measurement location (x,y) measured at an arbitrary coordinate, e.g., $(x_O, y_O)$ by projecting that location back to the point of origin on cornea 126. This can be explained mathematically using FIG. 1D. For simplicity, the explanation will assume that the error is only in the plane of the figure, i.e., the plane defined by $y=y_O$, although it is quite straightforward mathematically to extend the analysis to include errors the y-dimension. The quantation of the line L tracing the propagation of the wavefront element measured at $(x_O, y_O)$ in the $z_O$ reference plane from the corneal surface to the reference plane is:

$$L(x) = z_0 - \frac{(x - x_0)}{\delta W(x_0, y_0)/\delta x} \quad (3)$$

If the corneal surface in the plane of the figure is described by the expression $S(x_O, y_O)$, then the point of origin for the wavefront element in question can be found by finding the point of intersection between $L(x)$ and $S(x,y_O)$. Mathematically, this requires finding the value x' that satisfies $L(x')=S(x_O, y_O)$. The error $E_x(x_O, y_O)$ then is given as $E_x(x_O, y_O)=x'-x_O$. Extending the analysis to consider errors in the y-direction would yield a similar expression for $E_Y$ where $E_Y(x_O, y_O)=y'-y_O$. If significant, these transverse errors can be compensated for by laterally displacing the aberration correction calculated at each (x,y) coordinate by the amounts $E_X(x,y)$ and $E_Y(x,y)$ In the case of human corneas, the transverse error under most circumstances will be negligible. The error will be zero at the origin where the corneal tissue and reference plane 131 are tangent. For human corneas, the tissue is approximately spherical with a radius of curvature of approximately 7.5–8.0 mm. The corrective treatment radius is typically no more than 3 mm, and local wavefront radius of curvature will almost always exceed 50 mm (a 20 diopter refractive error). The transverse error E at a 3 mm treatment radius for a local wavefront radius of curvature of 50 mm is less than 40 mm.

For certain ophthalmic procedures, wavefront analysis can also be used repetitively during the corrective procedure to provide useful feedback information. One example of such use would be in cataract surgery where wavefront analysis could be performed on the eye following placement of an intra-ocular lens implant (IOL). The analysis could help identify whether the appropriate refractive power IOL has been inserted, or whether a different refractive power IOL should be used. Another example of repetitive wavefront analysis would be during keratoplastic procedures where the cornea of the eye is deliberately distorted by altering the mechanical tension around the periphery thereof. Here, repetitive wavefront analysis could be used to refine the degree of induced tension change at each point around the cornea thereby providing the tool to obtain, optimum surface curvature for best visual acuity.

In order to perform wavefront analysis in a manner compatible with corrective procedures such as those described above, the amount of spatial separation of component portions of wavefront 130 relative to the corresponding component portions of a planar or ideal wavefront must be measured. It is the system and method of the present invention that allows such separation to be objectively and accurately measured for even substantially aberrated eyes including those exhibiting severe defects such as severe myopia or hyperopia.

For the evaluation or measurement portion of the present invention, the patient's pupil should ideally be dilated to approximately 6 millimeters or more, i.e., the typical size of a human pupil in low light. In this way, the eye is evaluated while it is using the greatest area of the cornea so that any correction developed from such measurement takes into account the largest usable corneal area of the patient's eye. (A lesser amount of the cornea is used in daylight where the pupil is considerable smaller, e.g., on the order of 3 millimeters.) Dilation can be brought about naturally by implementing the measurement portion of the present invention in a low light environment such as a dimly lit room. Dilation can also be induced through the use of pharmacologic agents.

Figure 2:
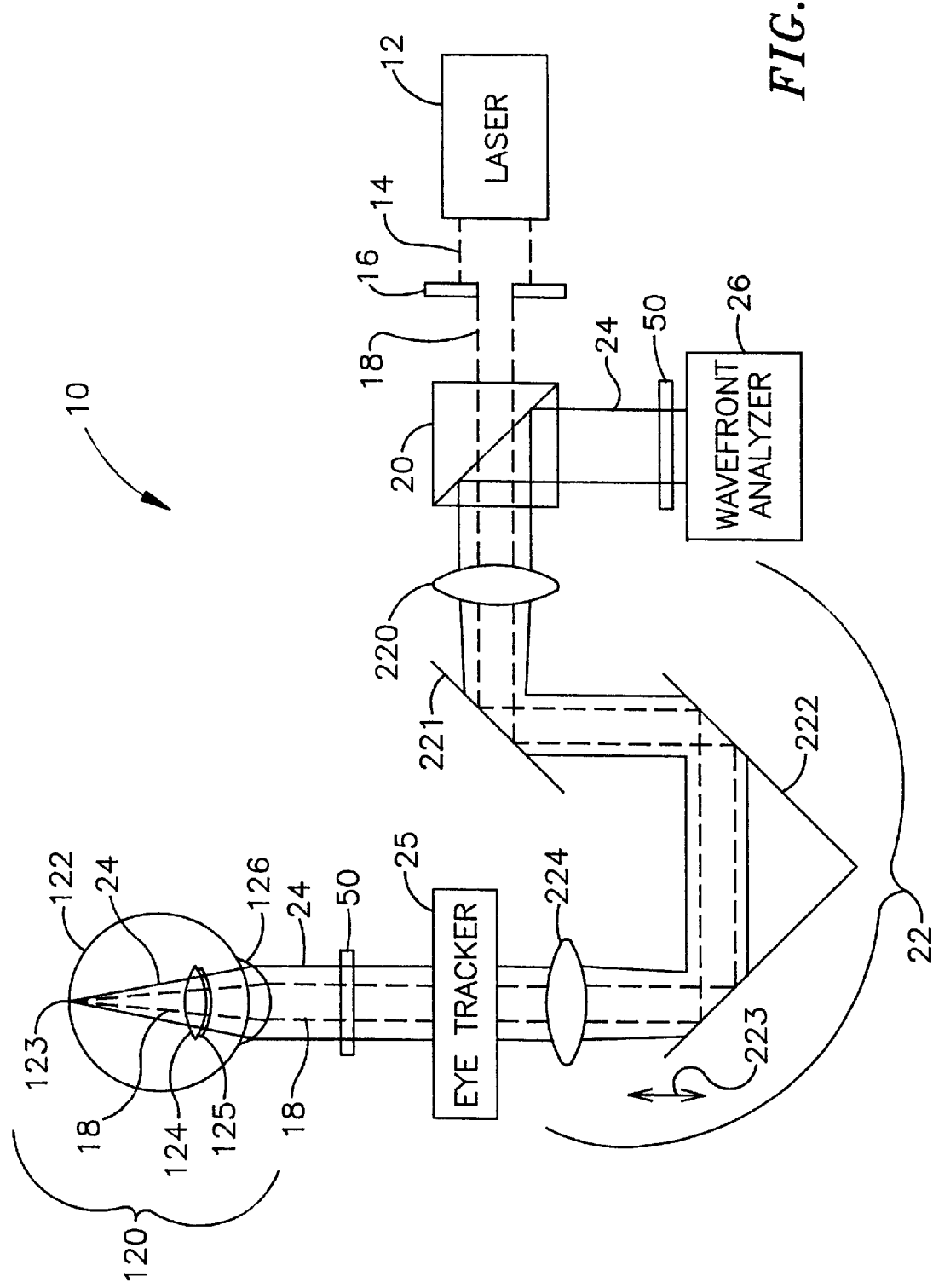
FIG. 2 is a simplified schematic of the system for determining ocular aberrations in accordance with the essential features of the present invention.

Referring now to FIG. 2, a simplified schematic of the system of the present invention depicting its essential elements is shown and referenced generally by numeral 10. System 10 includes laser 12 for generating the optical radiation used to produce a small-diameter laser beam. Laser 12 is typically a laser generating collimated laser light (represented by dashed lines 14) of a wavelength and power that is eye-safe. For ophthalmic applications, appropriate wavelengths would include the entire visible spectrum from approximately 400–710 nanometers and the near infrared spectrum from approximately 710–1000 nanometers. While operation in the visible spectrum is generally preferable (since these are the conditions in which the eye operates), the near infrared spectrum may offer advantages in certain applications. For example, the patient's eye may be more relaxed if the patient does not know measurement is taking place. Regardless of the wavelength of the optical radiation, power should be restricted in ophthalmic applications to eyesafe levels. For laser radiation, appropriate eye-safe exposure levels can be found in the U.S. Federal Performance Standard for Laser Products. If the analysis is to be performed on an optical system other than the eye, the examination wavelength range logically should incorporate the intended performance range of the system.

To select a small-diameter collimated core of laser light 14, an iris diaphragm 16 can be used to block all of laser light 14 except for laser beam 18 of a size desired for use by the present invention. In terms of the present invention, laser beam 18 can have a diameter in the range of approximately 0.5–4.5 millimeters with 1–3 millimeters being typical. A badly aberrated eye requires a smaller diameter beam while an eye with only slight aberrations can be evaluated with a larger diameter beam. Depending on the output divergence of laser 12, a lens (not shown) can be positioned in the beam path to optimize collimation.

Laser beam 18 is a polarized beam that is passed through a polarization sensitive beam splitter 20 enroute to being directed to a focusing optical train 22. Optical train 22 operates to focus laser beam 18 through the optics of eye 120 (e.g., cornea 126, pupil 125 and lens 124) to the back of the eye's retina 122. (It is to be understood that lens 124 may not be present for a patient that has undergone a cataract procedure, however, this does not affect the present invention.) In the illustrated example, optical train 22 images laser beam 18 as a small spot of light at or near the eye's fovea centralis 123 where the eye's vision is most acute. Note that the small spot of light could be reflected off another portion of retina 122 in order to determine aberrations related to another aspect of one's vision. For example, if the spot of light were reflected off the area of retina 122 surrounding the fovea centralis 123, aberrations specifically related to one's peripheral vision could be evaluated. In all cases, the spot of light is sized to form a near-diffraction limited image on retina 122. Thus, the spot of light produced by laser beam 18 at fovea centralis 123 does not exceed approximately 100 micrometers in diameter and, typically, is on the order of 10 micrometers.

The diffuse reflection of laser beam 18 back from retina 122 is represented in FIG. 2 by solid lines 24 indicative of the wavefront of radiation that passes back through eye 120. Wavefront 24 impinges on and is passed through optical train 22 enroute to polarization sensitive beam splitter 20. Wavefront 24 is depolarized relative to laser beam 18 due to reflection and refraction as wavefront 24 comes off retina 122. Accordingly, wavefront 24 is turned at polarization sensitive beam splitter 20 and directed to a wavefront analyzer 26 such as a Hartmann-Shack (H-S) wavefront analyzer. In general, wavefront analyzer 26 measures the slopes of wavefront 24, i.e., the partial derivatives with respect to x and y, at a number of (x,y) transverse coordinates. This partial derivative information is then used to reconstruct or approximate the original wavefront with a mathematical expression such as a weighted series of Zernike polynomials.

The purpose of the above-specified polarizations states for incident laser beam 18 and beamsplitter 20 is to minimize the amount of stray laser radiation reaching the sensor portion of wavefront analyzer 26. In some situations, stray radiation may be sufficiently small when compared to the radiation returning from the desired target (e.g., retina 122) so that the above polarization specifications are unnecessary.

The present invention is able to adapt to a wide range of vision defects and as such achieves a new level of dynamic range in terms of measuring ocular aberrations. Dynamic range enhancement is accomplished with optical train 22 and/or the wavefront sensor portion of wavefront analyzer 26 as will now be explained.

In the illustrated embodiment, optical train 22 includes a first lens 220, a flat mirror 221, a Porro mirror 222 and a second lens 224 all of which lie along the path of laser beam 18 and wavefront 24. First lens 220 and second lens 224 are identical lenses maintained in fixed positions. Porro mirror 222 is capable of linear movement as indicated by arrow 223 to change the optical path length between lenses 220 and 224. However, it is to be understood that the present invention is not limited to the particular arrangement of flat mirror 221 and Porro mirror 222 and that other optical arrangements could be used between lenses 220 and 224 to change the optical path length therebetween.

The "zero position" of Porro mirror 222 can be identified by replacing eye 120 in FIG. 2 by a broad beam source (not shown) of collimated light to simulate a perfect plane wave. Such a source could be realized by a laser beam expanded by a beam telescope to the diameter that will cover the imaging plane of wavefront analyzer 26 and adjusting Porro mirror 222 until wavefront analyzer 26 detects the light as being collimated. Note that the changes in optical path length brought about by Porro mirror 222 can be calibrated in diopters to provide an approximate spherical dioptric correction as will be explained further below.

Figure 3:
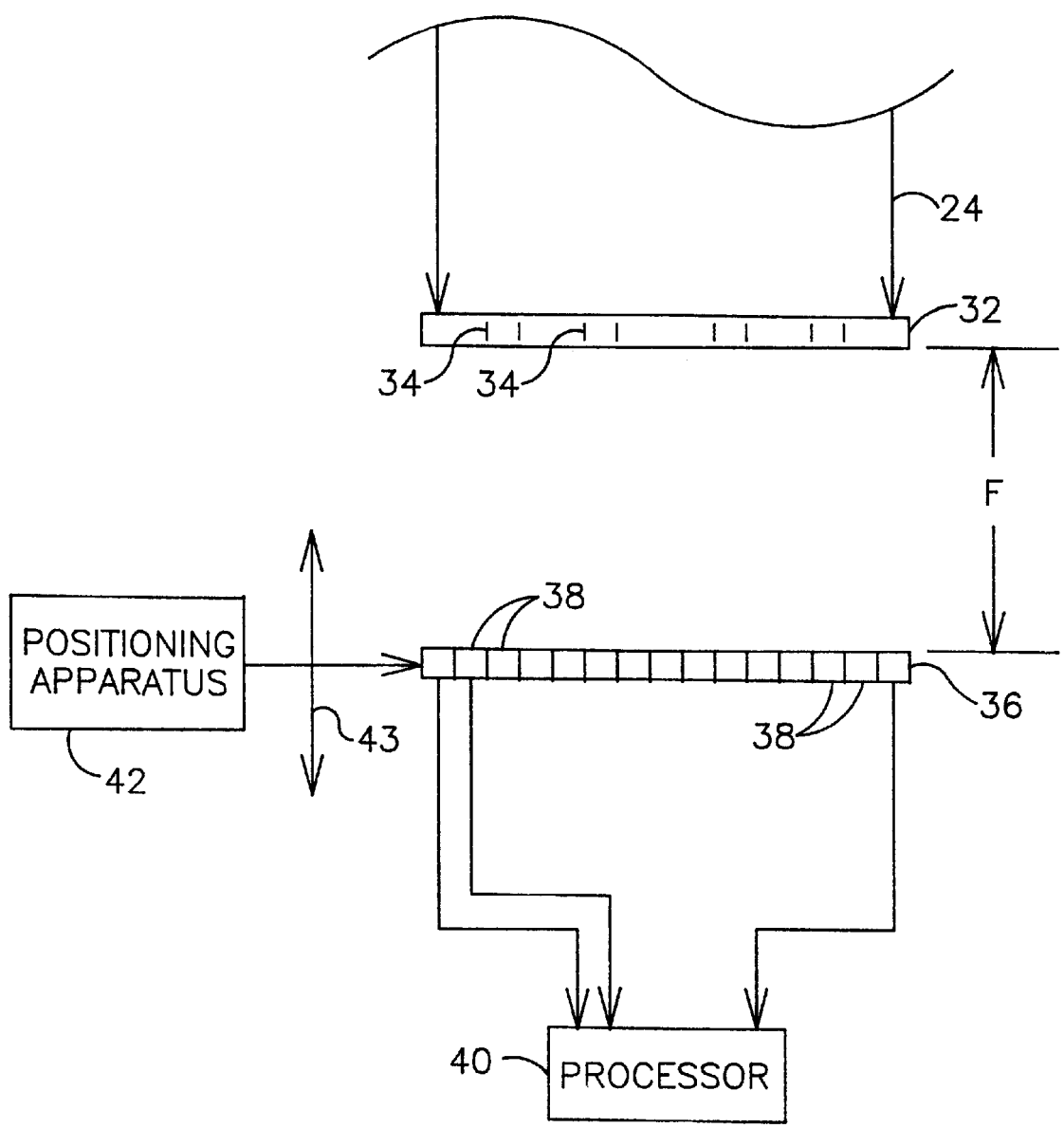
FIG. 3 is a schematic of one embodiment of a Hartmann Shack wavefront analyzer used in the present invention.

The dynamic range of system 10 can be further improved by utilizing a preferred embodiment wavefront analyzer to include an improved wavefront sensor arrangement. One such wavefront sensor arrangement will now be explained with the aid of FIGS. 3 and 4. In FIG. 3, the wavefront analyzer includes an opaque imaging plate 32 having an array of holes 34 passing therethrough, a planar array 36 of light-sensitive cells such as charge coupled device cells 38, and a processor 40 coupled to planar array 36 of cells 38. The combination of plate 32 and planar array 36 comprises the unique wavefront sensor of this embodiment. Plate 32 is maintained parallel to and spaced apart a separation distance F from planar array 36. As will be explained further below, separation distance F can be varied to adjust the gain of the sensor. To do this, planar array 36 is coupled to a positioning apparatus 42, e.g., a conventional motorized linear positioner having precise movement capability, that can adjust the position of planar array 36 relative to plate 32 to change separation distance F as indicated by arrow 43. With respect to the array of holes 34, each of holes 34 is of equal size and shape with a circle being typical owing to its ease of manufacture. In the illustrated example, a square array geometry is used for array of holes 34 although other array geometries can be used.

Figure 4:
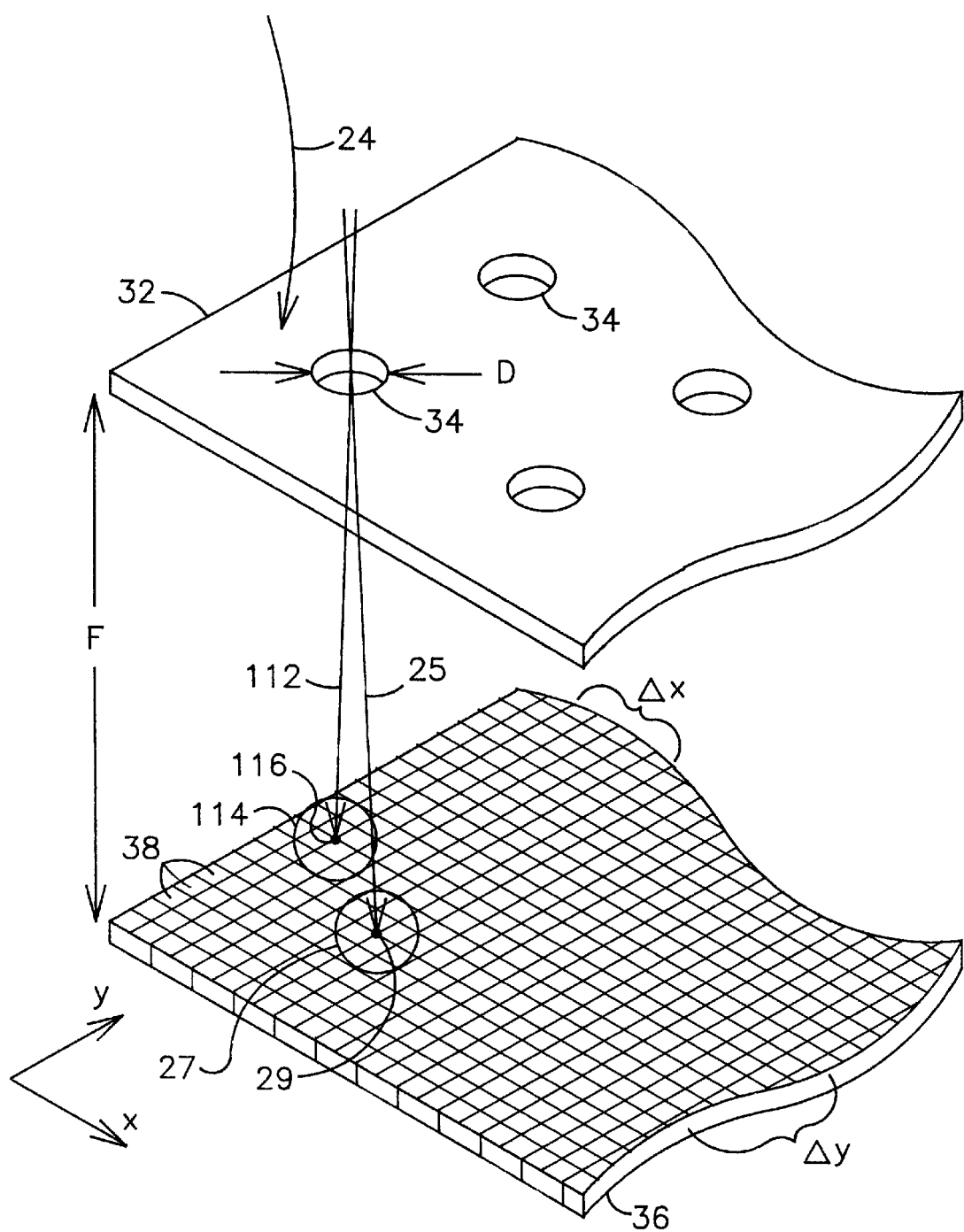
FIG. 4 is a perspective view of a portion of the pinhole imaging plate and planar array of light-sensitive cells comprising the wavefront sensor from the embodiment of FIG. 3 where the deflection of a wavefront piece associated with an aberrated eye is shown in comparison with a wavefront piece associated with a calibration or planar wavefront.

As shown in FIG. 4, when wavefront 24 impinges on plate 32, a piece or portion of wavefront 24, indicated by arrow 25, passes through hole 34 to illuminate planar array 36. To a first order, the resulting image formed by each such wavefront piece 25 is a positive shadow of the respective hole 34. However, diffraction does occur in a way determined by the diameter D of each hole 34, the wavelength A of the light source (i.e., wavefront 24) and the separation distance F between plate 32 and planar array 36. The value F is varied by positioning apparatus 42 to adjust the gain based on the particular patient as will be explained further below.

Note that the function provided by plate 32 with holes 34 could also be accomplished using a solid plate or film made from a light-sensitive material such as a photolithographic film. In such a case, the array of holes 34 would be replaced by an array of shaped light transmissive apertures through which light passes when impinging thereon. The remainder of such a plate or film would be impervious to light. The advantage achieved by such an embodiment is that the light transmissive apertures could easily be made to conform to any desired shape.

Regardless, of how each wavefront piece 25 is generated, the present invention measures the amount of angular deflection of each wavefront piece 25 relative to a wavefront piece that would result from a planar wavefront. This is best seen in FIG. 4 where the calibration or planar wavefront of light results in a wavefront piece represented by arrow 112 (normal to plate 32) that illuminates a geometric spot 114 on planar array 36. In contrast, assuming wavefront 24 represents a distorted wavefront as described above, wavefront piece 25 will exhibit an amount of angular deflection relative to (calibrating) wavefront piece 112. The angular deflection causes wavefront piece 25 to illuminate a geometric spot 27 on planar array 36 that is offset from (calibrating) spot 114. In terms of the present invention, the amount of offset is measured relative to the centroids 116 and 29 of spots 114 and 27, respectively. In the two dimensions of planar array 36, centroid 29 is (typically) deflected in both the x and y directions of array 36. Thus, the angular deflection in each of the x and y directions is given by $\Delta x/F$ and $\Delta y/F$, respectively.

In the preferred embodiment, lenses 220 and 224 are identical as mentioned above. However, in certain applications it may be desirable to magnify or minify the wavefront at the wavefront sensor. This can be accomplished by using lenses 220 and 224 of different focal lengths and adjusting the apparatus dimensions accordingly. For ophthalmic evaluation, the object plane of the apparatus should ideally be tangent to the corneal surface which can be achieved by a variety of means. Thus, each point at the object plane of optical train 22 very nearly corresponds to the same point on the cornea (although since the cornea is curved, there will be a slight lateral displacement). Plate 32 (or the imaging plane of any wavefront sensor portion) of wavefront analyzer 26 is positioned at the focal plane of lens 220. In this way, the object plane is always imaged on plate 32 in direct correspondence with the wavefront image emerging from cornea 126. This will be true regardless of the optical path length between lenses 220 and 224. There are several advantages to this structure, one of which is that there are very good planar arrays of light-sensitive cells that are commercially available to image an area corresponding to the 6 millimeter central circular region of the cornea. Additional advantages will now be explained.

The purpose of plate 32 (or the imaging plane of any wavefront sensor portion of wavefront analyzer 26) is to break wavefront 24 into wavefront pieces that can each be measured independently (in terms of propagation direction) at planar array 36. Since in the preferred embodiment optical train 22 does not magnify or reduce the image in the object plane, a point at the object plane corresponds to the same point at the image plane of optical train 22. With Porro mirror 222 set at its "zero position," the direction each piece of wavefront 24 is traveling at the object plane is reproduced exactly at the image plane of wavefront analyzer 26. For example, if a wavefront piece at a location in the object plane was traveling away from the optical axis at an angle of 20° with respect to the optical axis that is perpendicular to the object plane, the wavefront piece at the same location in the image plane will also be traveling away from the optical axis at an angle of 20°.

Note that a person who is myopic will produce a wavefront such that the wavefront pieces isolated by plate 32 will converge toward the center of planar array 36. A hyperopic person will produce a wavefront such that the wavefront pieces isolated by plate 32 diverge. Thus, a person with a significant vision error becomes difficult to evaluate because wavefront pieces can either overlap (myopia) at planar array 36 or spill off (hyperopia) planar array 36.

In the present invention, there are three ways of compensating for such severe aberrations. The first way is to utilize a wavefront sensor with sufficiently small light-sensitive cells 38 and sufficiently large holes 34 (or any other transmissive aperture). In this way, measurement of each wavefront piece can be performed to an acceptable accuracy using a small value for F. The second way is to move planar array 36 along the optical axis to change the separation distance F to plate 32. For a person with a severe aberration, planar array 36 is positioned close to plate 32 to keep the projected wavefront pieces well separated and on planar array 36. For a mild aberration, planar array 36 can be moved to increase the separation distance F to plate 32 to make a more accurate measurement. The advantage of moving planar array 36 to change the separation distance F to plate 32 is that the wavefront analysis is easily achieved for any position. The third way of compensating for severe aberrations in the present invention is to change the optical path length between lenses 220 and 224. Moving Porro mirror 222 will not affect where the wavefront hits plate 32, but will change the angular deflections at which the projected wavefront pieces pass through plate 32, i.e., $\Delta x/F$ and $\Delta y/F$. Decreasing the optical path length between lenses 220 and 224 will tend to pull the wavefront pieces toward the center of planar array 36 thereby compensating for hyperopia. Increasing the optical path length between lenses 220 and 224 will tend to spread the wavefront pieces toward the edges of planar array 36 thereby compensating for myopia. The degree to which the angular deflection associated with each wavefront piece is altered is a linear function of its distance off the optical axis and the movement of Porro mirror 222 from its zero position.

Figure 5:
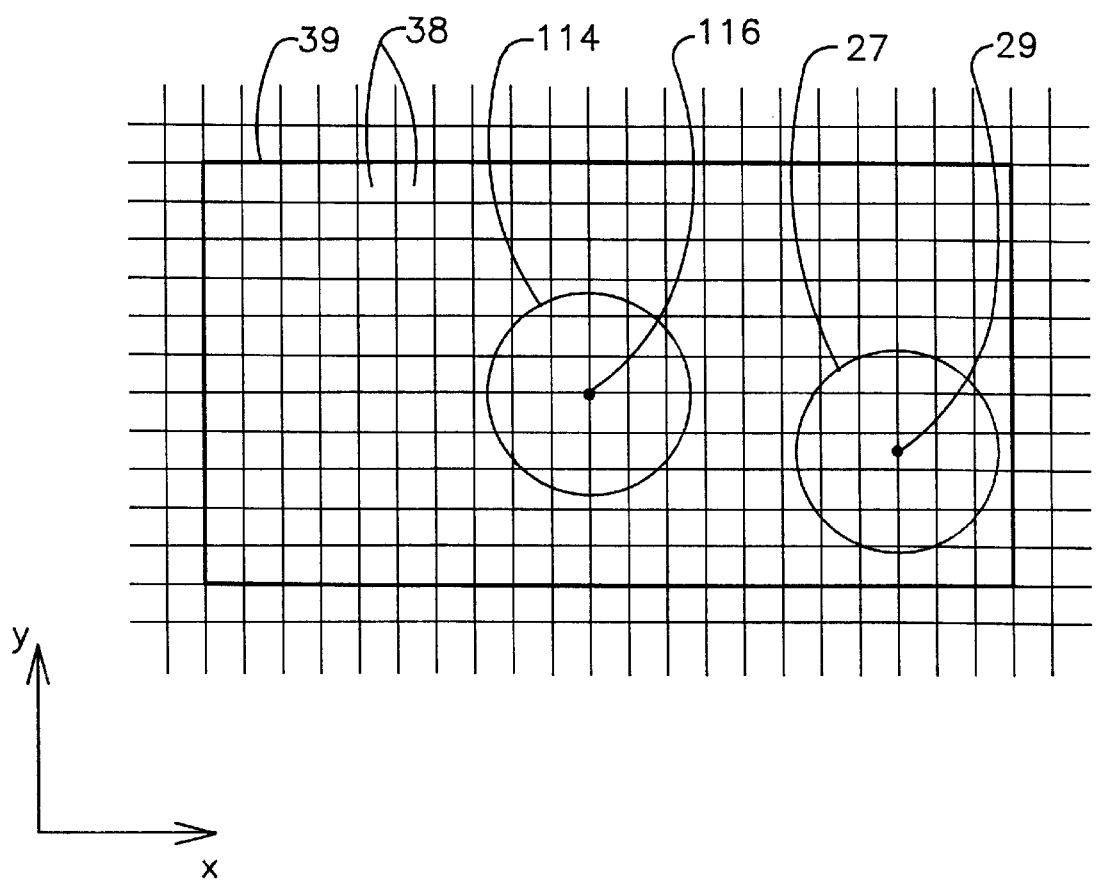
FIG. 5 is a plan view of a designated area on the planar array of light-sensitive cells associated with a corresponding hole.

In order to accurately determine the centroids of a spot of light impinging on array 36, it is necessary to provide a fine structure of cells 38 relative to a spot size. In other words, each spot must cover a plurality of cells 38. In the preferred embodiment, to determine the centroid of each spot unambiguously with respect to a spot caused by another one of holes 34, a unique number of cells 38 is assigned to each hole 34. The "assigned areas" are designated in FIG. 5 by the heavy grid lines 39. It is to be understood that grid lines 39 are not actual physical boundaries between cells 38 but are shown simply to illustrate the unique designated areas containing a plurality of cells 38. Other centroid strategies can be utilized that do not necessitate such partitioning of array 36.

Since the wavefront sensor of the present invention does not focus each wavefront piece to a minimum at the surface of array 36, a larger plurality of cells 38 are illuminated by each geometric spot so that the centroid of each spot can be determined to a greater precision than was previously possible.

Figure 6:
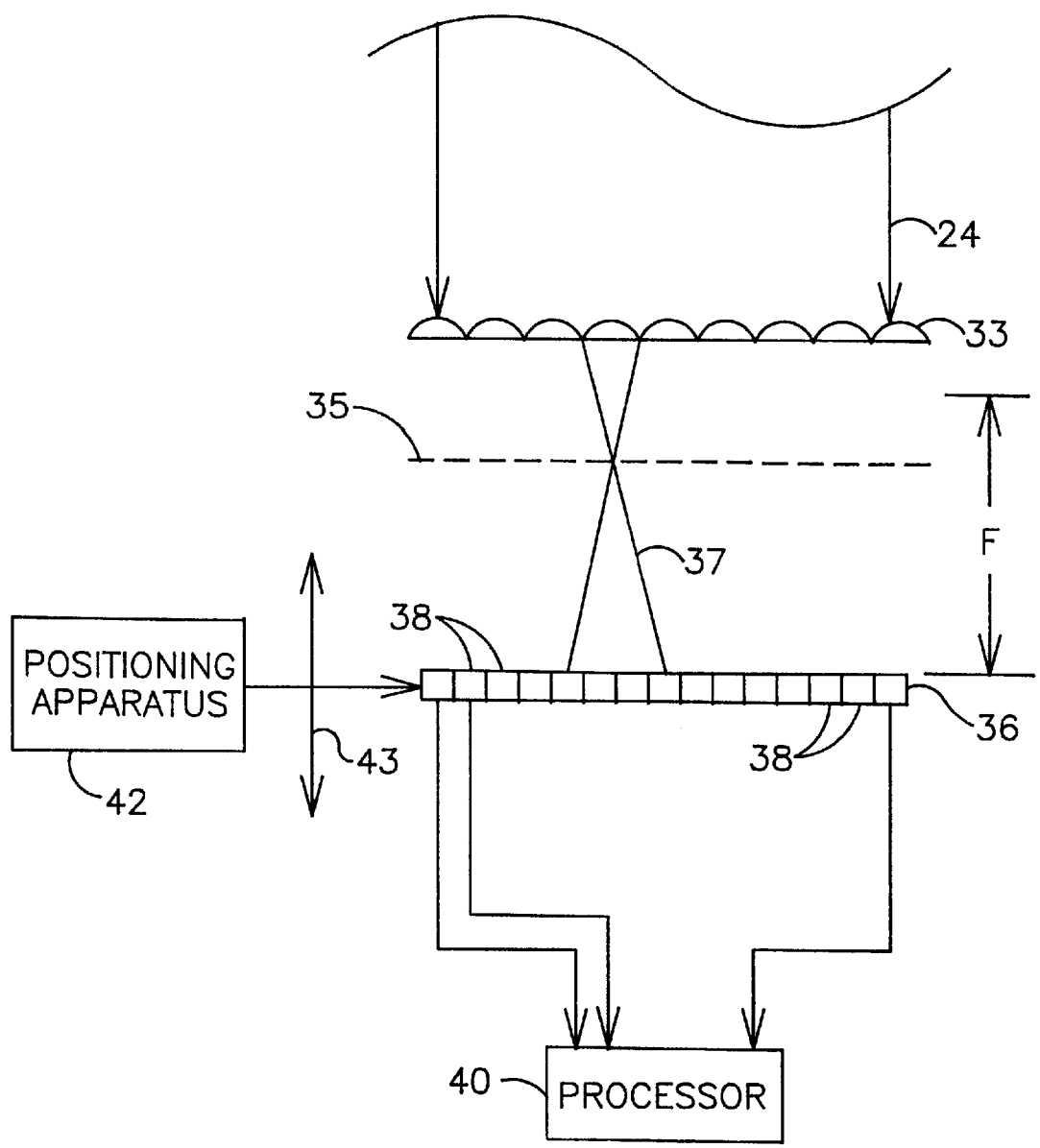
FIG. 6 is a schematic of another embodiment of a wavefront analyzer used in the present invention.

The present invention could also be practiced with a wavefront analyzer that replaced plate 32 (FIG. 3) with a two-dimensional array of identical spherical lenslets 33 as shown in FIG. 6. To achieve the advantages of the present invention, array 33 is positioned by positioning apparatus 42 such that separation distance F is independent of the focal length f that defines the focal plane of array 33 which is represented by dashed line 35. In other words, each wavefront piece (e.g., wavefront piece 37) passed through a subaperture of array 33 is reduced in size (e.g., diameter) but is not necessarily brought to a minimum focus at array 36 as it would be if separation distance F were equal to focal length f. Thus, in practice, array 33 is positioned to concentrate the light in each wavefront piece over an area for sufficient intensity on planar array 36, yet still illuminate a substantial plurality of cells 38 (as described above) for greatest accuracy in determining the deflection of the spot's centroid.

Regardless of the structure of the wavefront sensor, processor 40 computes each two-dimensional centroid of each spot generated by a wavefront 24. The amount of two-dimensional centroid shift (relative to the centroid of the calibrating spot) for each designated area associated with a corresponding hole 34 (or subaperture of array 33) is divided by the separation distance F to generate a matrix of local slopes of the wavefront, i.e., $\delta W(x,y)/\delta x$ and $\delta W(x,y)/\delta y$ at the (x,y), coordinates of the centers of holes 34. For simplicity, these will be indicated by $P(x,y)=\delta W(x,y)/\delta x$ and $Q(x,y)=\delta W(x,y)/\delta y$, respectively.

Numerous methods exist for using the partial derivative data to calculate the original (distorted) wavefront. One acceptable approach is that used by Liang et al. in the aforementioned paper where the wavefront is approximated using Zernike polynomials. This is a standard analytic technique described in numerous optics texts such as "Principles of Optics," by M. Born and E. Wolf, Pergamon Press, Oxford, England, 1964. By way of example, the Zernike polynomial approach will be discussed herein. However, it is to be understood that other mathematical approaches can be used in approximating the distorted wavefront.

Briefly, the wavefront $W(x,y)$ is expressed as a weighted sum of the individual polynomials $$W(x, y) = \sum_{i=0}^{n} C_i Z_i(x, y) \tag{4}$$

where $C_i$ are the weighting coefficients, and $Z_i(x,y)$ are the Zernike polynomials up to some order. The upper limit n on the summation is a function of the number of Zernike polynomials, i.e., the highest order, used to approximate the true wavefront. If m is the highest order used, then $$n=(m+1)(m+2)/2 \tag{5}$$

Derivation of the Zernike polynomials up to an arbitrary order n is described in numerous optical texts such as the aforementioned book by Born and Wolf.

One possible method of determining a centroid of a spot and calculation of the Zernike weighting coefficients will now be explained. The directions of the unit normals at the center of each hole 34 are based on the centroids of the spots on cells 38. Since each spot will illuminate a plurality of cells with varying intensity, a standard amplitude-weighted centroid calculation can be used to find the center of each spot. Each centroid must be measured twice, once for perpendicular collimated light, and again for the wavefront to be analyzed. Of course, all spots are imaged simultaneously during each exposure.

Multiple exposures may be used to check for improper eye alignment or eye movement during individual exposures. If eye movement during exposures cannot be analyzed successfully by acquiring multiple exposures, then system 10 can be augmented by the addition of an eye tracker 25. One possible placement of eye tracker 25 is shown in FIG. 2. However, it is to be understood that eye tracker 25 could be placed elsewhere in system 10. One such eye tracker is disclosed in the aforementioned U.S. patent application Ser. No. 08/232,615. In this way, wavefront analysis could be performed even during a limited amount of eye motion.

A one-time calibration exposure can also be used to determine the relative sensitivities of the individual cells. This is made in uniform collimated light with plate 32 removed. The responses of individual cells are then recorded.

For each light transmissive aperture (e.g., hole 34), the centroid in the collimated case serves as a dedicated origin for the particular hole. The shift from the "origin" for each hole to the centroid caused by wavefront 24 (as observed in this coordinate system) is determined by the direction of the wave surface corresponding to that hole. If $\Delta x(m,n)$ is the x-component of the (m,n)th centroid and F is the plate separation, then the P-value for the (m,n)th centroid is $$P(m,n)=\delta x(m,n)/\delta z=\Delta x(m,n)/F \tag{6}$$

The corresponding expression for Q is:

$$Q(m,n)=\delta y(m,n)/\delta z=\Delta y(m,n)/F \tag{7}$$

Thus, each $P(m,n)$ and $Q(m,n)$ represents the partial derivatives of $W(x,y)$ with respect to x and y for the (x,y) coordinates of each hole 34. For an m-order Zernike approximation of the original wavefront, the experimentally determined P's and Q's are then used in the following equations to calculate the appropriate $C_i$ weighting coefficients as follows:

$$P(m, n) = \frac{\delta W(x, y)}{\delta x} = \sum_{i=0}^{n} C_i \frac{\delta Z_i(x, y)}{\delta x} \tag{8}$$

$$Q(m, n) = \frac{\delta W(x, y)}{\delta x} = \sum_{i=0}^{n} C_i \frac{\delta Z_i(x, y)}{\delta x} \tag{9}$$

By using a least-squares approx(m,n)/δzach to minimize the error between the actual wavefront slopes on the left hand side in the above equations and the Zernike approximations on the right hand side, optimal values for the weighting coefficients can be obtained.

In one possible approach to calculating a centroid $(x_c,y_c,)$ each hole 34 is assigned its dedicated area of the array 36 or $(i_{m,n}\pm\Delta i, j_{m,n}\pm\Delta j)$. This square of many light-sensitive cells is large enough that neighboring hole images never encroach, and all illumination from this hole is contained. The square contains $4\Delta i * \Delta j$ cells.

If array 36 is designated $c_{k,1}=(x_c(i,j),y_c(i,j))$, k, 1=0 . . . $2\Delta 1$, $2\Delta j$, and the spacing on centers is $\Delta x=\Delta y=d$, the measured cell responses are $V(k,1)$ and the relative responsivities are $R(k,I)$, then the x-component $x_c$, a function of i,j is represented by $$x_c(i,j)=[\Sigma_{k,1}V(k,1)* R(k,1)*d*k]/[\Sigma_{k,1}V(k,1)*R(k,1)] \tag{10}$$

and the y-component $y_c$, as a function of i,j is represented by $$y_c(i,j)=[\Sigma_{k,1}V(k,1)*R(k,1)*d*1]/[\Sigma_{k,1}V(k,1)*R(k,1)] \tag{11}$$

Then, if $(x_{c0}(i,j), y_{c0}(i,j))$ is the "origin centroid" for the (i,j) hole, i.e., made in perpendicular collimated light, and $(x_{cw}(i,j), y_{cw}(i,j))$ is the corresponding centroid found for the wavefront to be measured, then the relative centroid shift $(x_{cr}(i,j), Y_{cr}(i,j))$ is found as $$x_{cr}(i,j)=x_{cw}(i,j)-x_{c0}(i,j) \tag{12}$$

$$y_{cr}(i,j)=y_{cw}(i,j)-y_{c0}(i,j) \tag{13}$$

The values $P(i,j)$ and $Q(i,j)$ are determined from $$P(i,j)=x_{cr}(i,j)/F \tag{14}$$

and $$Q(i,j)=y_{cr}(i,j)/F \tag{15}$$

The surface partial derivatives $P(i,j)$ and $Q(i,j)$ for the array of hole centers of plate 32 are next used to calculate the appropriate Zernike polynomial weighting coefficients to describe the original wavefront $W(x,y)$. This will now be explained by way of illustration for a 7×7 square array of holes 34. However, it is to be understood that other sizes and shapes of hole arrays could be used.

First, a 1×98 matrix (i.e., column vector) PQ(k) is formed as $$PQ(k)=P(7i+j), j=0 \ldots 6, i=0 \ldots 6, k=0 \ldots 48 \tag{16}$$

$$PQ(k)=Q(7i+j), j=0 \ldots 6, i=0 \ldots 6, k=49 \ldots 98 \tag{17}$$

with j cycling for each i, i.e., PQ (18)=P(2,5).

The matrix PQ is multiplied from the left with a transition matrix TM to get the matrix C as follows $$C=TM*PQ \tag{18}$$

where TM is a 98 wide by 14 high matrix and C is a 1 wide by 14 high matrix or column vector. C is the matrix $C_k$ k=1, . . . , 14 such that, to a least square error, $$W(x,y) = \Sigma_k C_k * Z_k(x,y) \tag{19}$$

and TM is calculated for a given aperture, e.g., a 6 millimeter pupil aperture.

The functions $Z_k(x,y)$ in equation (19) are the Zernike polynomials. There is no standard convention as to their sequence. Thus, for consistency, it is important that the same sequence is used to produce the set $C_k$ that was chosen for deriving the matrix TM. They occur in groups of the same order, which is the highest exponent in the group, with the total number of members in an order increasing with the order. For example, in a fourth order analysis, orders up to and including 4 are used (less $Z_0$—the single member of order 0 that is the constant 1 which describes the reference position of the group in the z direction). Since wavefront 24 is moving along z (at the velocity of light), this "piston term" describes only an arbitrary offset in Z, and this term may be ignored. The first 5 orders (0, 1, . . . ,4) contain 15 functions including the piston term.

Thus, in the illustrated example, 14 values of $C_k$ are calculated as coefficients of 14 Zernike polynomials. By way of example, one such order used to calculate TM is given in Table 1, which includes both the Zernike functions and their partial derivatives.

TABLE 1

ZERNIKE (X,Y) POLYNOMIAL EXPANSION THROUGH ORDER 4

| | |
|---|---|
| Polynomial Order 0 | |
| Z(0) | +1 |
| dZ(0)/dx | 0.0 |
| DZ(0)/dy | 0.0 |
| Polynomial Order 1 | |
| Z(1) | +y |
| dZ(1)/dx | 0.0 |
| dZ(1)/dy | +1 |
| Z(2) | +x |
| dZ(2)/dx | +1 |
| dZ(2)/dy | 0.0 |
| Polynomial Order 2 | |
| Z(3) | $+1 + 2y^2 + 2x^2$ |
| dZ(3)/dx | +4x |
| dZ(3)/dy | +4y |
| Z(4) | +2xy |
| dZ(4)/dx | +2y |
| dZ(4)/dy | +2x |
| Z(5) | $-y^2 + x^2$ |
| dZ(5)/dx | +2x |
| dZ(5)/dy | −2y |
| Polynomial Order 3 | |
| Z(6) | $-2y + 3y^3 + 3x^2y$ |
| dZ(6)/dx | +6xy |
| dZ(6)/dy | $-2 + 9y^2 + 3x^2$ |
| Z(7) | $-2x + 3xy^2 + 3x^3$ |
| dZ(7)/dx | $-2 + 3y^2 + 9x^2$ |
| dZ(7)/dy | +6xy |
| Z(8) | $-y^3 + 3x^2y$ |
| dZ(8)/dx | +6xy |
| dZ(8)/dy | $-3y^2 + 3x^2$ |
| Z(9) | $-3xy^2 + x^3$ |
| dZ(9)/dx | $-3y^2 + 3x^2$ |
| dZ(9)/dy | −6xy |
| Polynomial Order 4 | |
| Z(10) | $+1 - 6y^2 + 6y^4 - 6x^2 + 12x^2y^2 + 6x^4$ |
| dZ(10)/dx | $-12x + 24xy^2 + 24x^3$ |
| dZ(10)/dy | $-12y + 24y^3 + 24x^2y$ |
| Z(11) | $-6xy + 8xy^3 + 8x^3y$ |
| dZ(11)/dx | $-6y + 8y^3 + 24x^2y$ |
| dZ(11)/dy | $-6x + 24xy^2 + 8x^3$ |
| Z(12) | $+3y^2 - 4y^4 - 3x^2 + 4x^4$ |

TABLE 1-continued

ZERNIKE (X,Y) POLYNOMIAL EXPANSION THROUGH ORDER 4

| | |
|---|---|
| dZ(12)/dx | $-6x + 16x^3$ |
| dZ(12)/dy | $+6y - 16y^3$ |
| Z(13) | $-4xy^3 + 4x^3y$ |
| dZ(13)/dx | $-4y^3 + 12x^2y$ |
| dZ(13)/dy | $-12xy^2 + 4x^3$ |
| Z(14) | $+y^4\ 6x^2y^2 + x^4$ |
| dZ(14)/dx | $-12xy^2 + 4x^3$ |
| dZ(14)/dy | $+4y^3 - 12x^2y$ |

The choice of sequencing the Zernike polynomials dictates the interpretations of the $C_k$ in equation (19) and therefore the order of terms in the TM matrix. Hence, the TM matrix must be calculated after the choice is made. The development of the TM matrix for the illustrated example will be explained below.

Note that the fourth order analysis is only an example and is not the only possibility. A Zernike analysis can be done to any order. In general, the higher the order, the more accurate the result over the tested points. However, an exact polynomial fit over the tested points is not necessarily desirable. Such fits have the typical disturbing property that, unless the surface itself happens to be an exact polynomial of order no higher than that used for the surface fit, forcing an exact fit at separated points often causes wild swings between fitted points. That is, in polynomial surface fitting, an exact fit at a finite number of points can yield a poor average fit for a general function. For ophthalmic application of the system as described above, computer simulations suggest that a sixth order Zernike analysis may yield the best results.

Calculation of the $\Delta z(x,y)$ optical path difference information from the Zernike reconstruction of the wavefront is accomplished simply by subtracting a constant from the Zernike approximation. The value of the constant will depend on the desired characteristics of $\Delta z(x,y)$. Depending on the method chosen to correct the aberrations (e.g., laser ablation, lens addition, etc.) it may, for example, be desirable to set either the maximum, mean or minimum value in $\Delta z(x,y)$ equal to zero.

The development of the transition matrix TM will now be explained for the illustrated example of a 7×7 array of holes in plate 32. At each point $(x_i, y_j)$, the tangents of the components of the normal are $P(x_i, y_j)$ and $Q(x_i, y_j)$ where $$P(x_i, y_j) = \delta W(x_i, y_j)/\delta x \tag{20}$$

and $$Q(x_i, y_j) = \delta W(x_i, y_j)/\delta y \tag{21}$$

Combining these with equation (11), $$P(x_i, y_j) = \Sigma_k C_k \delta W(x_i, y_j)/\delta x \tag{22}$$

and $$Q(x_i, y_j) = \Sigma_k C_k \delta W(x_i, y_j)/\delta y \tag{23}$$

each applicable to 49 (i,j) combinations. These are combined into a single column vector PQ that is 98 elements high, i.e., a 98×1 matrix. Defining two matrices $C_k$ (14 high×1 wide) and $M_{k(i,j)}$ (14 wide×98 high)

$$(M_{k,(i,j)}) = \delta Z_k(x_i, y_j)/\delta x;\ \delta Z_k(x_i, y_j)/\delta y \tag{24}$$

where the x-derivatives are the first 49 rows and the y-derivatives are the last 49 rows. Then, equation (19) can be rewritten as the matrix equation $$(PQ) = (M)(C) \quad (25)$$

where the top 49 rows of M are the $\delta W(x_i, y_j)/\delta y$.

The expression in equation (25) gives the normal components in terms of the Zernike coefficients for a surface described by the array of 14 C's. These are exact, but it is not guaranteed that the actual total surface can be described by such an array of coefficients. Accordingly, if it is assumed that the description is within an acceptable tolerance, i.e., tolerating the errors that remain after least square error determination, then equation (26) can be considered to define the column vector C implicitly in terms of the mathematical matrix M and the measured vector PQ, both of which are known. The method of effecting the solution under the minimization condition is as follows.

First, equation (25) is multiplied on the left by $M^T$, the transpose of M such that $$(M^T)(PQ) = (M^T)(M)(C) = (S)(C) \quad (26)$$

where $$S \equiv M^T M \quad (27)$$

is a square and symmetric matrix, e.g., of dimensions 14×14 (with each element the sum of 98 products). Such a matrix has an inverse unless the determinant of its coefficients is zero. Since this is based on the Zernike polynomials alone, and they are all independent of each other, the determinant is non-zero, so that an inverse $S^{-1}$ is defined. Next, equation (25) is multiplied on the left by $S^{-1}$ to yield $$(S^{-1})(M^T)(PQ) = (S^{-1})(S)(C) = (I)(C) = C \quad (28)$$

Then, the mathematical transition matrix (independent of measurement) is $$(TM) = (S^{-1})(M^T) \quad (29)$$

and the "best fit" array of C's from the measured PQ's can be produced by the simple matrix multiplication $$(C) = (TM)(PQ) \quad (30)$$

To evaluate the eye unambiguously, all spots illuminating planar array 36 due to a wavefront 24 must be incident on planar array 36 simultaneously. This is achieved by pulsing or shuttering the laser source (i.e., laser 12) such that pulse duration is less than the saccadic motion interval of the eye, i.e., a few milliseconds. Alternatively, the laser source could be left on continuously and wavefront 24 could be shuttered to appear as a wavefront pulse of a duration that is less than saccadic motion of the eye. Accordingly, as shown in FIG. 2, shutter 50 could be positioned in the path of laser beam 18 before eye 120 or in the path of wavefront 24 before wavefront analyzer 26.

Figure 7:
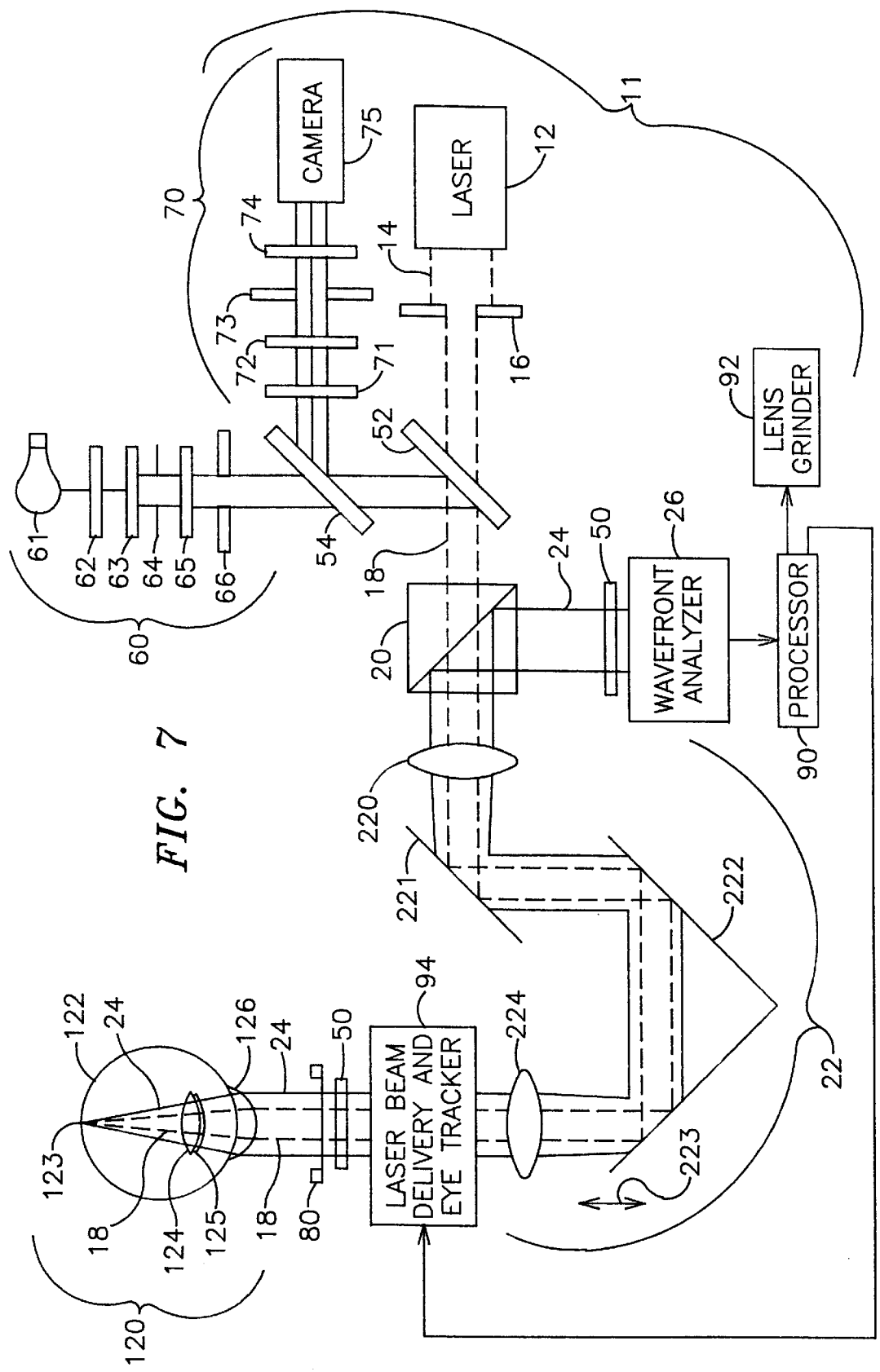
FIG. 7 is a schematic view of an embodiment of the present invention suitable for ophthalmic use.

An implementation of the present invention suitable for clinical use is shown schematically in FIG. 7 and is referenced generally by numeral 11. Like reference numerals are used to describe elements that are the same as those described above with respect to system 10. Accordingly, the like elements and their functions will not be described further.

A dichroic beam splitter 52 is interposed between beam splitter 20 and optical train 22 to introduce fixation target optics 60 and observation optics 70 into system 11 which are optically separated from one another by 50/50 beam splitter 54. Functionally, fixation target optics provide eye 120 with visible light in the shape of a target. The visible light generated by fixation target optics 60 is reflected by dichroic beam splitter 50 and directed through optical train 22.

It is to be understood that fixation target optics 60 can be implemented in a variety of fashions. By way of example, one such embodiment is shown and includes visible light source 61, light diffuser 62, target 63, field stop 64, lens 65 and iris 66. Light source 61 and light diffuser 62 are used to provide uniform illumination of fixation target 63. Field stop 64, lens 65, and iris 66 are used in conjunction with optical train 22 to present a clear image of the fixation target to (patient) eye 120.

Functionally, observation optics 70 allows a technician to view and document the eye evaluation procedure. While a variety of implementations of observation optics 70 are possible, one such implementation is shown by way of example. In FIG. 7, observation optics 70 includes field lens 71, lens 72, iris 73, lens 74, and camera 75. A ring illuminator 80 is placed in front of eye 120 to illuminate same for observation and/or filming purposes.

The output from wavefront analyzer 26, e.g., the Zernike expansion of equation (19), can be used in a variety of ways. For example, the output could be used to continually or periodically monitor the progress or effects of an ophthalmic procedure. The output could also be used to develop an optical correction for eye 120. The optical correction will make wavefront 24 appear approximately as a plane wave. As described above, the optical correction can be implemented in a variety of ways. In each case, the output of wavefront analyzer 26 is input to a processor 90 which converts the Zernike expansion of equation (19) into a form suitable for being implemented as one of the possible optical corrections. (The functions of processor 90 could also be implemented at processor 40 of wavefront analyzer 26.)

Figure 8:
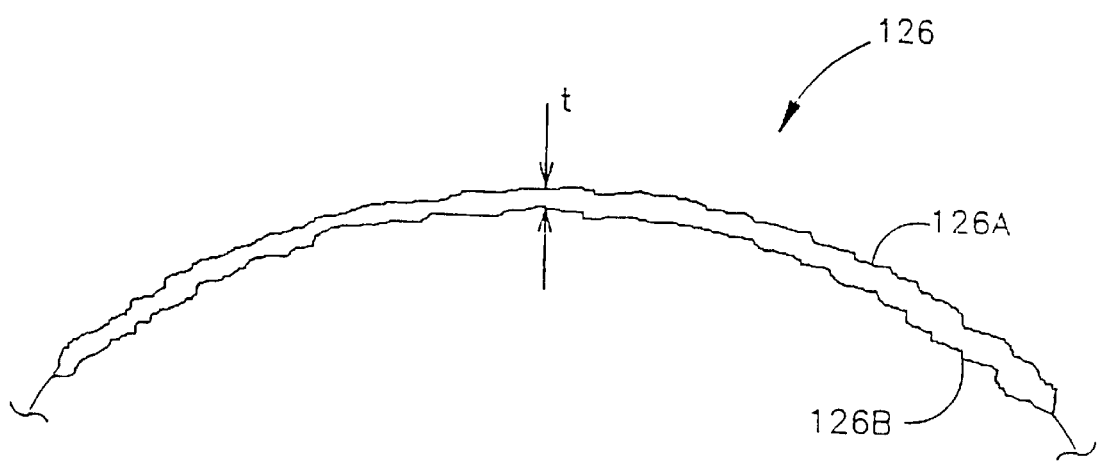
FIG. 8 is a side view of a cornea showing a thickness of corneal material to be ablated as an optical correction generated by the present invention.

Processor 90 could use some of the Zernike coefficients from the expansion of equation (19) to generate a standard sphero-cylindrical correction for lens grinder 92 to produce a conventional optical lens, e.g., a lens for glasses, a contact lens, etc. Processor 90 could also divide the Zernike reconstruction of the aberrated wavefront by the index of refraction of cornea 126 minus 1, to calculate the amount of corneal material to be ablated at each corresponding (x,y) location on the cornea. The amount of corneal material at each location is input to a laser beam delivery system that typically has eye tracking capability 94 such as described in the afore-mentioned U.S. patent application Ser. No. 08/232, 615. Laser beam delivery and eye tracker 94 is placed in line with the optical axis of system 11. The eye tracker portion of this element allows system 11 to respond unwanted eye motion. Laser beam delivery and eye tracker 94 would typically focus short pulses or "shots" of ablating laser light at cornea 126 or eye 120 to remove the specified thickness t of material at each location. This is shown diagrammatically in FIG. 8 where the uncorrected surface of cornea 126 is referenced by numeral 126A and the corrected surface of cornea 126 after ablation is referenced by numeral 126B.

In accordance with the present invention, ablation thickness t is specified across the aperture of the cornea measured, e.g., the 6 millimeter circle to which the eye's pupil was dilated during the measurement of the eye. Outside the prescribed treatment circle, a tapering blend zone of partial ablation may be added to minimize severe changes in corneal curvature and hence lessen regression. Laser beam delivery system 94 removes thickness t to achieve the optical correction, i.e., corrected cornea surface 126B. Note that the optical correction is not concerned with the ultimate corneal topography, but instead removes corneal material to achieve an optical correction that takes into account all ocular aberrations of the eye. This is important because the shape of the corneal surface can be independent of the correction required because the eye's vision depends on numerous factors besides corneal curvature. Hence, the best corneal surface topography for optimal vision may be far from regular in that it must compensate for the errors in the eye's other surfaces. Thus, it is apparent that the present invention can be used to provide corneal surface corrections other than the conventional spherical and/or cylindrical corrections.

The advantages of the present invention are numerous. A totally objective approach is presented for measuring ocular aberrations. The approach is effective for a wide range of vision defects. Accordingly, the present invention will be of great utility in a wide variety of clinical applications. For example, the calculated Zernike coefficients can be used to develop a completely objective lens prescription or a corneal correction that could be accomplished with laser ablation. In addition, each of the wavefront sensor embodiments provides for a greater degree of accuracy over the prior art with respect to measuring wavefront deflections. Further, the present wavefront sensor can be adjusted in terms of gain simply by adjusting the separation distance between the imaging plane of the sensor and the planar array of light-sensitive cells.

The objective measurement of the present invention will also find great utility for a large variety of applications in which the "patient" is unable to provide feedback as required by conventional eye diagnosis. For example, the present invention could be used to evaluate the eyes of any patient not possessed of demonstrative communicative skills, e.g., babies, animals, dead specimens, as well as any constructed optical system, since the present invention is an objective analysis not requiring any assessment from the "subject." All that is necessary is for the subject's eye to be properly positioned so that proper optical access to the eye can be obtained.

The present invention could also be used in the area of identification should it be determined that each eye's Zernike coefficients are unique. Then, the present invention would find great utility in the fields of law enforcement, credit card/bank security, or any other field where positive identification would be beneficial.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

That which is claimed is:

1. A system comprising:
   an energy source for generating a beam of optical radiation;
   focusing optics disposed in the path of said beam for directing said beam through a focusing optical system having a rear portion thereof functioning as a diffuse reflector, wherein said beam is diffusely reflected back from said rear portion as a wavefront of radiation that passes through said focusing optical system to impinge on said optics, said optics projecting said wavefront in direct correspondence with said wavefront impinging on said optics, said focusing optics comprising
   a first lens maintained in a first fixed position in the path of said beam and said wavefront;
   a second lens maintained in a second fixed position in the path of said beam and said wavefront; and
   an arrangement of optical elements disposed between said first lens and said second lens in the path of said beam and said wavefront, said arrangement of optical elements being adjustable for changing the optical path length between said first lens and said second lens; and
   a wavefront analyzer disposed in the path of said wavefront projecting from said optics for calculating distortions of the wavefront as an estimate of aberrations of said focusing optical system.

2. A system as in claim 1 wherein said energy source comprises:
   a collimated laser for generating collimated laser light; and
   an iris diaphragm disposed in the path of said collimated laser light to project a collimated core of said collimated laser light, wherein said collimated core is said beam of radiation having a diameter in the range of approximately 0.5 millimeters to approximately 4.5 millimeters.

3. A system as in claim 1 wherein said wavefront analyzer includes a wavefront sensor for dividing said wavefront into a plurality of optical radiation beams, wherein a focal plane of said first lens is at said wavefront sensor, and wherein a focal plane of said second lens is at an object plane of said focusing optical system.

4. A system as in claim 1 wherein said focusing optical system is an eye and wherein said wavefront analyzer includes a wavefront sensor for dividing said wavefront into a plurality of optical radiation beams, wherein a focal plane of said first lens is at said wavefront sensor, and wherein a focal plane of said second lens is at the pupil of said eye.

5. A system as in claim 1 wherein said wavefront analyzer is a Hartmann-shack wavefront analyzer.

6. A system as in claim 1 wherein said focusing optical system is any eye and further comprising means for causing said beam to occur as a pulse of duration that is less than the saccadic motion interval of said eye.

7. A system as in claim 1 wherein said focusing optical system is any eye and further comprising means for causing said wavefront to appear to said wavefront analyzer as a pulse of duration that is less than the saccadic motion interval of said eye.

8. A system as in claim 1 wherein said focusing optical system is any eye and further comprising a fixation target generator for generating visible light in the shape of a target, said fixation target generator arranged so that said visible light is directed through said optics wherein said visible light can be viewed by said eye.

9. A system as in claim 1 further comprising a converter for converting said distortions to an optical correction which, if placed in the path of said wavefront, causes said wavefront to appear approximately as a plane wave.

10. A system as in claim 9 wherein said converter converts said distortions to a lens prescription, and wherein said optical correction is achieved by a lens based on said lens prescription.

11. A system as in claim 9 wherein said optical system is an eye and wherein said converter converts said distortions to an amount of corneal material of complex geometric shape to be ablated from said eye, said system further comprising a laser beam delivery system for bombarding said eye with a plurality of small-diameter laser beam pulses of a wavelength and power that ablates said corneal material, wherein said optical correction is achieved by the removal of said amount of corneal material.

12. A system as in claim 11 wherein said laser beam delivery system further includes an eye tracker for monitoring motion of said eye and for adjusting the positions of said plurality of small-diameter laser beam pulses in correspondence with said motion.

13. A system as in claim 9 wherein said optical system is an eye and wherein said converter converts said distortions to a prescribed alteration of corneal surface curvature of said eye, and wherein said optical correction is achieved by the reshaping of said corneal surface curvature of said eye based on said prescribed alteration.

14. A system as in claim 1 wherein said optical system is an eye and further comprising an eye tracker for monitoring motion of said eye.

15. A system comprising:

an energy source for generating a beam of radiation;

optics disposed in the path of said beam for directing said beam through a focusing optical system having a rear portion thereof functioning as a diffuse reflector, wherein said beam is diffusely reflected back from said rear portion as a wavefront of radiation that passes through said focusing optical system to impinge on said optics, said optics projecting said wavefront in direct correspondence with said wavefront impinging on said optics; and a wavefront analyzer disposed in the path of said wavefront projecting from said optics for calculating distortions of the wavefront as an estimate of aberrations of said focusing optical system, said wavefront analyzer comprising a plate that is light impervious except for an array of light transmissive apertures that allow impinging light to pass therethrough, said plate disposed in the path of said wavefront wherein portions of said wavefront pass through said array of light transmissive apertures;

a planar array of light-sensitive cells arranged parallel to and spaced apart from said plate by a selected distance, wherein each of said portions of said wavefront passing through one of said array of light transmissive apertures illuminates a geometric shape covering a unique plurality of cells from said planar array of cells;

a processor coupled to said planar array of cells for calculating said distortions based on a centroid of each said geometric shape; and means for adjusting said selected distance between said plate and said planar array of cells.

16. A system as in claim 15 wherein each light transmissive aperture in said array of light transmissive apertures is of equal size.

17. A system as in claim 15 wherein each light transmissive aperture insaid array of light transmissive apertures is circular.

18. A system as in claim 15 wherein said array of light transmissive apertures is a square array.

19. A system as in claim 15 wherein said radiation is optical radiation and wherein said focusing optics comprises:

a first lens maintained in a first fixed position in the path of said beam and said wavefront;

a second lens maintained in a second fixed position in the path of said beam and said wavefront; and an arrangement of optical elements disposed between said first lens and said second lens in the path of said beam and said wavefront, said arrangement of optical elements being adjustable for changing the optical path length between said first lens and said second lens.

20. A system comprising:

an energy source for generating a beam of optical radiation;

focusing optics disposed in the path of said beam for directing said beam through a focusing optical system having a rear portion thereof functioning as a diffuse reflector, wherein said beam is diffusely reflected back from said rear portion as a wavefront of radiation that passes through said focusing optical system to impinge on said optics, said optics projecting said wavefront in direct correspondence with said wavefront impinging on said optics, said focusing optics comprising a first lens maintained in a first fixed position in the path of said beam and said wavefront;

a second lens maintained in a second fixed position in the path of said beam and said wavefront; and an arrangement of optical elements disposed between said first lens and said second lens in the path of said beam and said wavefront, said arrangement of optical elements being adjustable for changing the optical path length between said first lens and said second lens; and a wavefront analyzer disposed in the path of said wavefront projecting from said optics for calculating distortions of the wavefront as an estimate of aberrations of said focusing optical system, said wavefront analyzer comprising a two-dimensional array of spherical lenslets that defines a focal plane that is a focal length away from said two-dimensional array of spherical lenslets, said two-dimensional array of spherical lenslets disposed in the path of said wavefront wherein portions of said wavefront pass through said two-dimensional array of spherical lenslets;

a planar array of light-sensitive cells arranged parallel to and spaced apart from said two-dimensional array of spherical lenslets by a selected distance independent of said focal length, wherein each of said portions of said wavefront passing through said two-dimensional array of spherical lenslets illuminates a geometric shape covering a unique plurality of cells from said planar array of cells;

a processor coupled to said planar array of CCD cells for calculating said distortions based on a centroid of each said geometric shape; and means for adjusting said selected distance between said two dimensional array of spherical lenslets and said planar array of cells.

21. A system as in claim 20 wherein said optics comprises:

a first lens maintained in a first fixed position in the path of said beam and said wavefront;

a second lens maintained in a second fixed position in the path of said beam and said wavefront; and an arrangement of optical elements disposed between said first lens and said second lens in the path of said beam and said wavefront, said arrangement of optical elements being adjustable for changing the optical path length between said first lens and said second lens.

22. An optical wavefront sensor, comprising:

a plate that is light impervious except for an array of light transmissive apertures that allow impinging light to pass therethrough, said plate disposed in the path of an optical wavefront wherein portions of said optical wavefront pass through said array of light transmissive apertures;

a planar array of lightsensitive cells arranged parallel to and spaced apart from said plate by a selected distance, wherein each of said portions of said optical wavefront passing through one of said array of light transmissive apertures illuminates a geometric shape covering a unique plurality of cells from said planar array of cells; and means for adjusting said selected distance between said plate and said planar array of cells.

23. An optical wavefront sensor as in claim 22 wherein each light transmissive aperture in said array of light transmissive apertures is of equal size.

24. An optical wavefront sensor as in claim 22 wherein each light transmissive aperture in said array of light transmissive apertures is circular.

25. An optical wavefront sensor as in claim 22 wherein said array of light transmissive apertures is a square array.

26. An optical wavefront sensor as in claim 22 further comprising a processor coupled to said planar array of cells for determining a centroid of each said geometric shape.

27. A method comprising the steps of:

generating a beam of optical radiation;

focusing said beam with focusing optics into an eye to image said beam as a focused spot forming a near-diffraction limited image at a back portion of the retina of said eye, wherein said beam is diffusely reflected back from the retina as a wavefront of radiation that passes through said eye;

allowing said wavefront to impinge on said focusing optics;

projecting, with said focusing optics, said wavefront in direct correspondence with said wavefront impinging on said focusing optics;

calculating distortions associated with said wavefront projecting from said focusing optics using a wavefront analyzer disposed in the path of said wavefront projecting from said focusing optics, wherein said wavefront analyzer includes a plate that is light impervious except for an array of light transmissive apertures that allow impinging light to pass therethrough, said plate disposed in the path of said wavefront wherein portions of said wavefront pass through said array of light transmissive apertures, and a planar array of light-sensitive cells arranged parallel to and spaced apart from said plate by a selected distance, wherein each of said portions of said wavefront passing through one of said array of light transmissive apertures illuminates a geometric shape covering a unique plurality of cells from said planar array of cells; and adjusting said selected distance to adjust the gain of said wavefront analyzer.

28. A method according to claim 27 wherein said step of generating comprises the steps of: producing collimated laser light; and selecting a collimated core of said collimated laser light as said beam of optical radiation having a diameter in the range of approximately 0.5 millimeters to approximately 4.5 millimeters.

29. A method according to claim 27 wherein said step of focusing comprises the steps of:

fixing a first lens in a first position in the path of said beam and said wavefront;

fixing a second lens in a second position in the path of said beam and said wavefront; and positioning an arrangement of optical elements between said first lens and said second lens in the path of said beam and said wavefront; and adjusting positions of said arrangement of optical elements to change the optical path length between said first lens and said second lens.

30. A method according to claim 29 wherein said wavefront analyzer includes a wavefront sensor for dividing said wavefront into a plurality of optical radiation beamed wherein said step of fixing said first lens includes the Step of locating a focal plane of said first lens at said wavefront sensor, and wherein said step of fixing said second lens includes the step of locating a focal plane of said second lens at the pupil of said eye.

31. A method according to claim 27 wherein said step of focusing comprises the steps of:

fixing a first lens in a first position in the path of said beam and said wavefront;

fixing a second lens in a second position in the path of said beam and said wavefront; and positioning an arrangement of optical elements between said first lens and said second lens in the path of said laser beam and said wavefront; and adjusting positions of said arrangement of optical elements to change the optical path length between said first lens and said second lens.

32. A method according to claim 27 further comprising the step of Shattering said beam such that a pulse is directed through said focusing optics said pulse having a duration that is less than the saccadic motion interval of said eye.

33. A method according to claim 27 further comprising the step of puttering said wavefront such that said wavefront appears to said wavefront analyzer as a pulse of duration that is less than the saccadic motion interval of said eye.

34. A method according to claim 27 further comprising the steps of: generating visible light in the shape of a target; and directing said visible light through said focusing optics wherein said visible light can be viewed by said eye.

35. A method according to claim 27 further comprising the step of converting said distortions to an optical correction which, if placed in the path of said wavefront, causes said wavefront to appear approximately as a plane wave.

36. A method according to claim 35 wherein said optical correction is in the form of a lens.

37. A method according to claim 35 wherein said optical correction is in the form of an amount of corneal material to be ablated from said eye.

38. A method according to claim 35 wherein said optical correction is in the form of prescribed alteration of corneal surface curvature of said eye.

39. A method according to claim 27 further comprising the step of dilating the pupil of said eye to a size achieved in a low-light environment, said step of dilating being accomplished prior to said steps of focusing, allowing and projecting.

40. A method according to claim 27 further comprising the Steps of: performing an ophthalmic procedure on said eye; and performing said steps of generating, focusing, allowing, projecting and calculating at least once after said ophthalmic procedure has commenced to monitor the effects of said ophthalmic procedure on said eye.

41. A method according to claim 27 wherein said step of calculating comprises the step of calculating Zernike coefficients associated with said distortions.

42. A method comprising the steps of:

generating a beam of optical radiation;

focusing said beam with focusing optics into an eye to image said beam as a focused spot forming a near-diffraction limited image at a back portion of the retina of said eye, wherein said beam is diffusely reflected back from the retina as a wavefront of radiation that passes through said eye;

allowing said wavefront to impinge on said focusing optics;

projecting, with said focusing optics, said wavefront in direct correspondence with said wavefront impinging on said focusing optics;

calculating distortions associated with said wavefront projecting from said focusing optics using a wavefront analyzer disposed in the path of said wavefront projecting from said focusing optics, wherein said wavefront analyzer includes a two-dimensional array of spherical lenslets that defines a focal plane that is a focal length away from said two-dimensional array of spherical lenslets, said two-dimensional array of spherical lenslets disposed in the path of said wavefront wherein portions of said wavefront pass through said two-dimensional array of spherical lenslets, and a planar array of lightsensitive cells arranged parallel to and spaced apart from said two-dimensional array of spherical lenslets by a selected distance not equal to said focal length, wherein each of said portions of said wavefront passing through said two-dimensional array of spherical lenslets illuminates a geometric shape covering a unique plurality of cells from said planar array of cells having an array of holes passing therethrough; and adjusting said selected distance to adjust the gain of said wavefront analyzer.

43. A method according to claim 42 wherein said step of focusing comprises the steps of: fixing a first lens in a first position in the path of said beam and said wavefront; fixing a second lens in a second position in the path of said beam and said wavefront; and positioning an arrangement of optical elements between said first lens and said second lens in the path of said beam and said wavefront; and adjusting positions of said arrangement of optical elements to change the optical path length between said first lens and said second lens.

* * * * *